US011931327B2

(12) United States Patent
Tsuji et al.

(10) Patent No.: US 11,931,327 B2
(45) Date of Patent: Mar. 19, 2024

(54) DRUG FOR RETINAL DEGENERATIVE DISEASE ASSOCIATED WITH PHOTORECEPTOR DEGENERATION

(71) Applicant: Daiichi Sankyo Company, Limited, Tokyo (JP)

(72) Inventors: Naoki Tsuji, Shinagawa-ku (JP); Masumi Ueno, Koto-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 601 days.

(21) Appl. No.: 16/628,232

(22) PCT Filed: Jul. 3, 2018

(86) PCT No.: PCT/JP2018/025122
§ 371 (c)(1),
(2) Date: Jan. 2, 2020

(87) PCT Pub. No.: WO2019/009265
PCT Pub. Date: Jan. 10, 2019

(65) Prior Publication Data
US 2020/0330415 A1 Oct. 22, 2020

(30) Foreign Application Priority Data
Jul. 4, 2017 (JP) .............................. 2017-131087

(51) Int. Cl.
| A61K 31/196 | (2006.01) |
| A61K 9/00 | (2006.01) |
| A61K 31/192 | (2006.01) |
| A61K 31/24 | (2006.01) |
| A61K 31/415 | (2006.01) |
| A61K 31/4436 | (2006.01) |
| A61K 49/00 | (2006.01) |
| A61P 27/02 | (2006.01) |
| C12N 5/079 | (2010.01) |
| G01N 33/50 | (2006.01) |

(52) U.S. Cl.
CPC ........ *A61K 31/196* (2013.01); *A01K 67/0275* (2013.01); *A61K 9/0048* (2013.01); *A61K 31/192* (2013.01); *A61K 31/24* (2013.01); *A61K 31/415* (2013.01); *A61K 31/4436* (2013.01); *A61K 49/0008* (2013.01); *A61P 27/02* (2018.01); *C12N 5/0621* (2013.01); *G01N 33/5058* (2013.01); *A01K 2217/05* (2013.01); *A01K 2227/40* (2013.01); *A01K 2267/0306* (2013.01)

(58) Field of Classification Search
CPC ... G01N 33/5058; C12N 5/0621; A61P 27/02; A01K 67/0275; A01K 2217/05; A01K 2227/40; A01K 2267/0306; A61K 31/196; A61K 9/0048; A61K 31/192; A61K 31/24; A61K 31/415; A61K 31/4436; A61K 49/0008
See application file for complete search history.

(56) References Cited

U.S. PATENT DOCUMENTS

| 2005/0009910 | A1 | 1/2005 | Hughes et al. | |
| 2007/0112032 | A1 | 5/2007 | Whitcup et al. | |
| 2009/0281184 | A1 | 11/2009 | Sawada et al. | |
| 2014/0121407 | A1* | 5/2014 | Muratake | A61P 35/02 |
| | | | | 562/450 |
| 2014/0187504 | A1 | 7/2014 | Chaturvedi | |

FOREIGN PATENT DOCUMENTS

| JP | 2007-513161 A | 5/2007 | |
| JP | 2007-528851 A | 10/2007 | |
| JP | 2014-517077 A | 7/2014 | |
| WO | 1998/018480 A1 | 5/1998 | |
| WO | 1998/045331 A2 | 10/1998 | |
| WO | WO-2005056010 A1 * | 6/2005 | ............. A61K 31/00 |
| WO | 2006/007314 A1 | 1/2006 | |
| WO | 2007/037188 A1 | 4/2007 | |

OTHER PUBLICATIONS

Shaomei Wang, et al, Non-Invasive Stem Cell Therapy in a Rat Model for Retinal Degeneration and Vascular Pathology, 5 PLOS ONE e9200 (Year: 2010).*
Hiroshi Keino, et al, Oral Administration of Retinoic Acid Receptor α/β-specific Ligand Am80 Suppresses Experimental Autoimmune Uveoretinitis, 52 Inv. Ophthal. Vis. Sci. 1548 (Year: 2011).*
Albane le Maire, et al, Retinoid Receptors and Therapeutic Applications of RAR/RXR Modulators, 12 Curr. Top. Med. Chem. 505 (Year: 2012).*
Partial Supplementary European Search Report dated Mar. 3, 2021, issued in corresponding Application No. 18827721.4, filed on Jul. 3, 2018, 13 pages.
International Search Report and Written Opinion of the International Searching Authority dated Oct. 2, 2018, Issued in corresponding Application No. PCT/JP2018/025122, filed Jul. 3, 2018, 29 pages.
Akimoto, M., "Regenerative Medicine: Toward Curative Therapy for Retinal Degenerative Diseases," Journal of the Eye 23(9):1153-1160, 2006.
Farrar, G.J., et al., "On the Genetics of Retinitis Pigmentosa and on Mutation-Independent Approaches to Therapeutic Intervention," The EMBO Journal 21(5):857-864, 2002.
Guadagni, V., et al., "Pharmacological Approaches to Retinitis Pigmentosa: A Laboratory Perspective," Progress in Retinal and Eye Research 48:62-81, 2015.

(Continued)

*Primary Examiner* — Sean M Basquill
(74) *Attorney, Agent, or Firm* — Christensen O'Connor Johnson Kindness PLLC

(57) ABSTRACT

An object of the present invention is to provide a medicine that can simply treat and/or prevent a retinal degenerative disease associated with photoreceptor degeneration, including retinitis pigmentosa. The solution is to provide an agent for treating and/or preventing a retinal degenerative disease associated with photoreceptor degeneration, containing a compound having a retinoic acid receptor agonistic activity (for example, tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene) or a salt thereof.

3 Claims, 5 Drawing Sheets

Specification includes a Sequence Listing.

(56) References Cited

OTHER PUBLICATIONS

He, Y., et al., "Recent Advances of Stem Cell Therapy for Retinitis Pigmentosa," International Journal of Molecular Sciences 15(8):14456-14474, 2014.

Kami, J., et al., "Retinoic Acid Receptor Agonist Am90 Inhibits Experimental Choroidal Neovascularization," Investigative Ophthalmology & Visual Science, vol. 45, No. 13, p. 1856, May 2004 (ARVO Annual Meeting Abstract).

Kelley, M.W., et al., "Retinoic Acid Promotes Differentiation of Photoreceptors In Vitro," Development 120(8):2091-2102, 1994.

Mendes, H.F., et al., "Mechanisms of Cell Death in Rhodopsin Retinitis Pigmentosa: Implications for Therapy," TRENDS in Molecular Medicine 11(4):177-185, Apr. 2005.

Tang, S., et al., "Experimental Studies of Effects of Retinoic Acid on the Proliferation of Retinal Cells," Chinese Journal of Ophthalmology 38(2):112-114, Feb. 2002.

Yu, H., et al., "Mobilizing Endogenous Stem Cells for Retinal Repair," Translational Research 163(4):387-398, Apr. 2014.

Written Opinion of the International Searching Authority dated Oct. 2, 2018, issued in corresponding International Application No. PCT/JP2018/025122, filed Jul. 3, 2018, 23 pages.

* cited by examiner

[Figure 1]
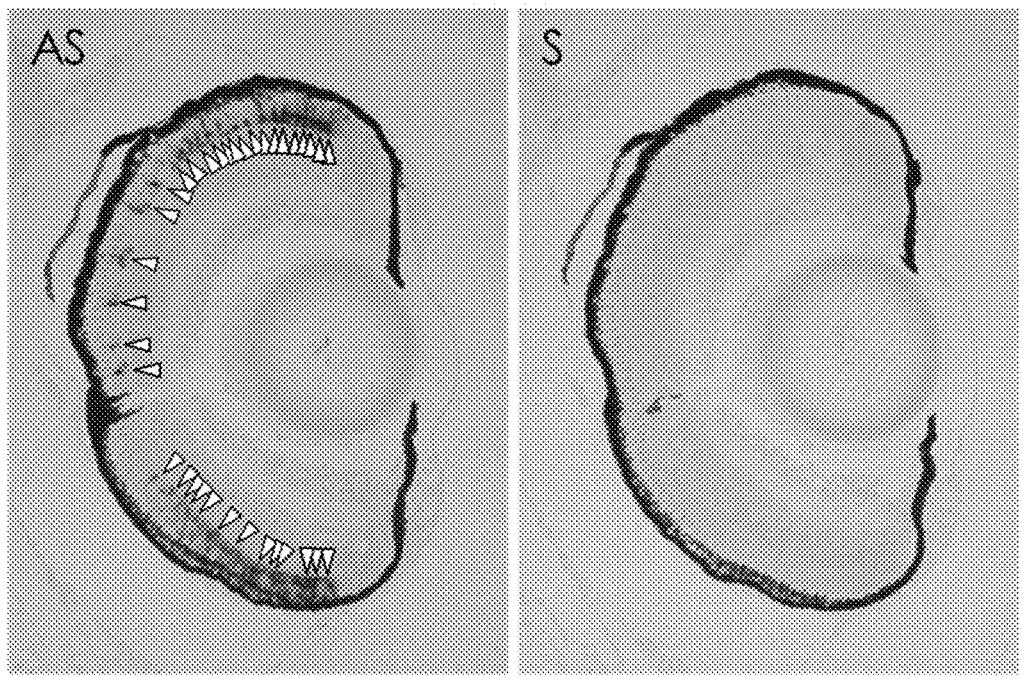
[Figure 2]
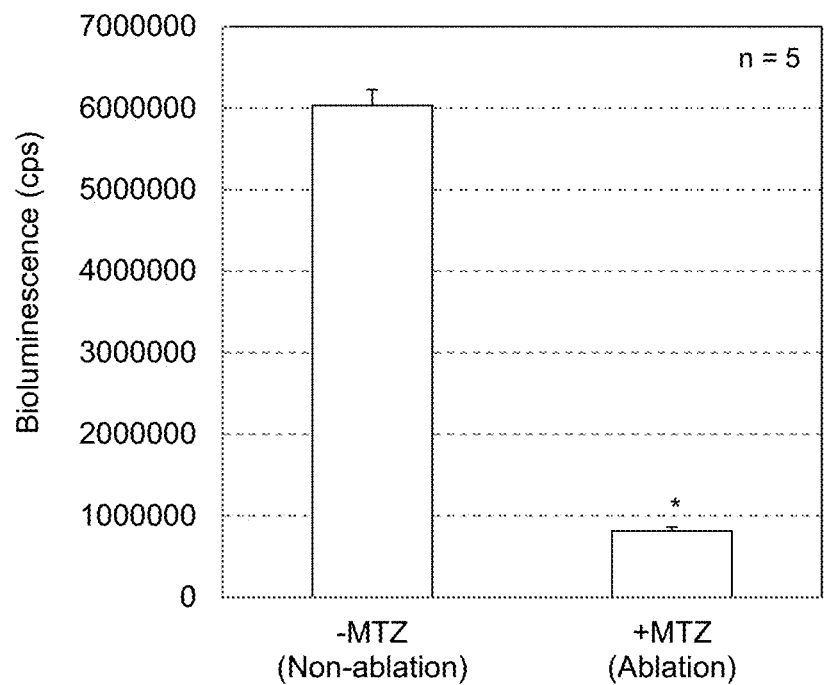

[Figure 3]
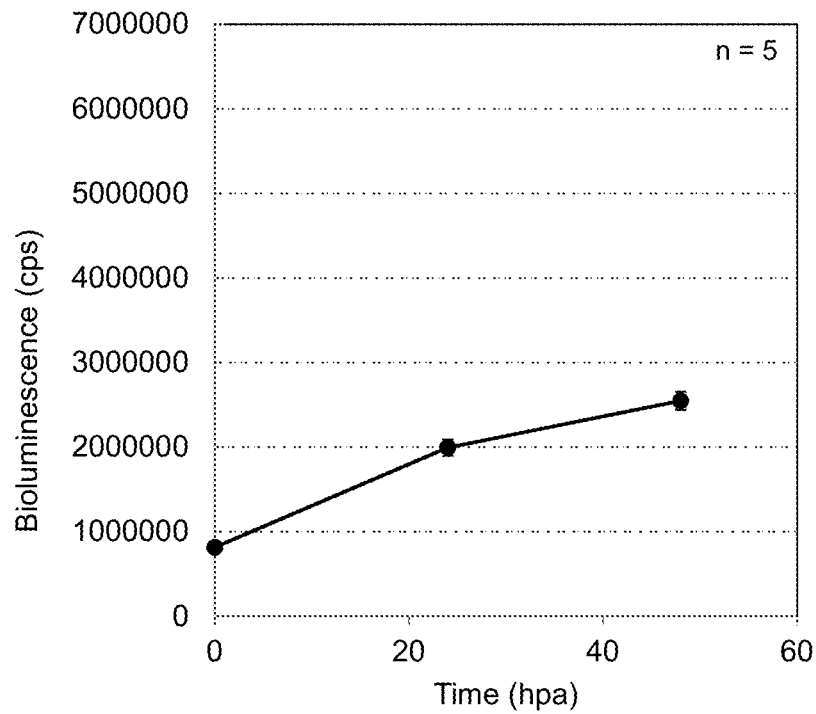
[Figure 4]
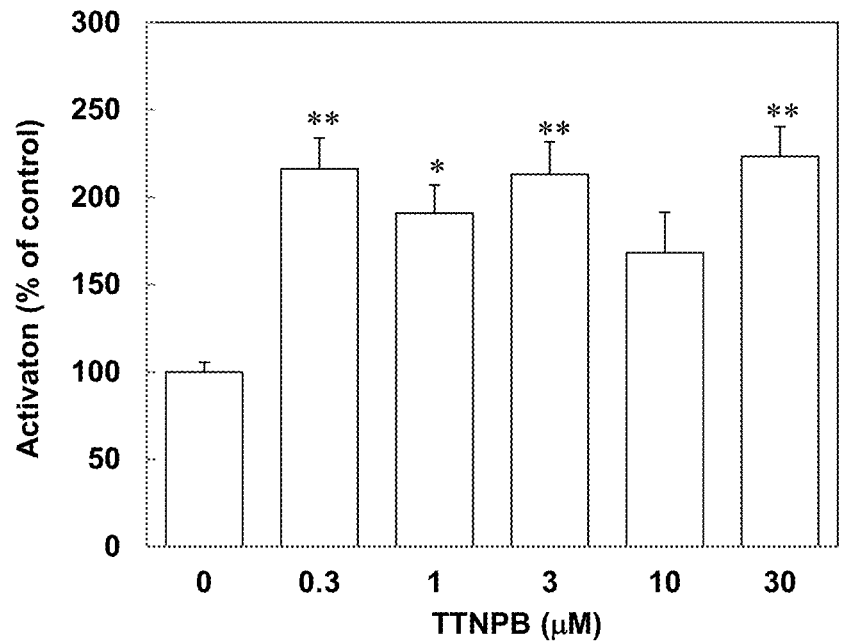

[Figure 5]
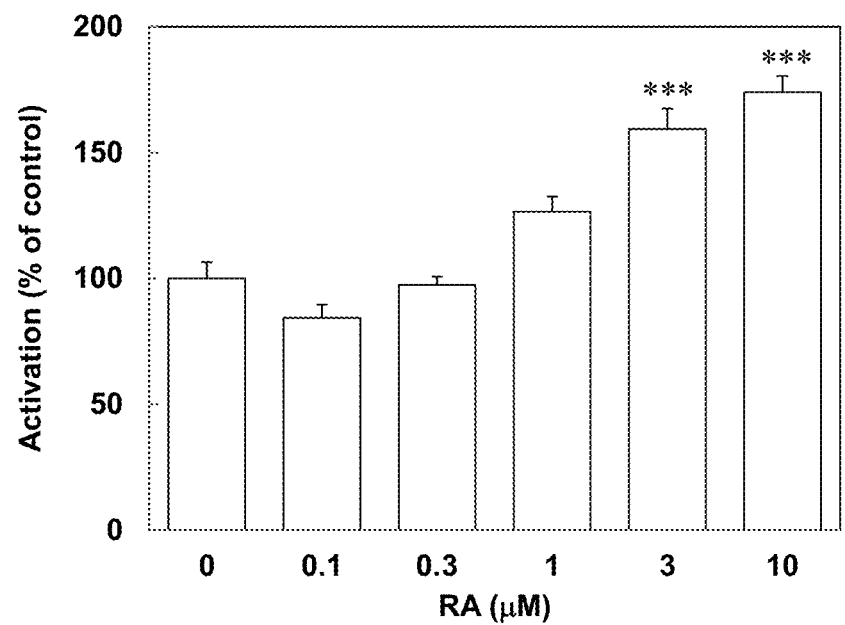
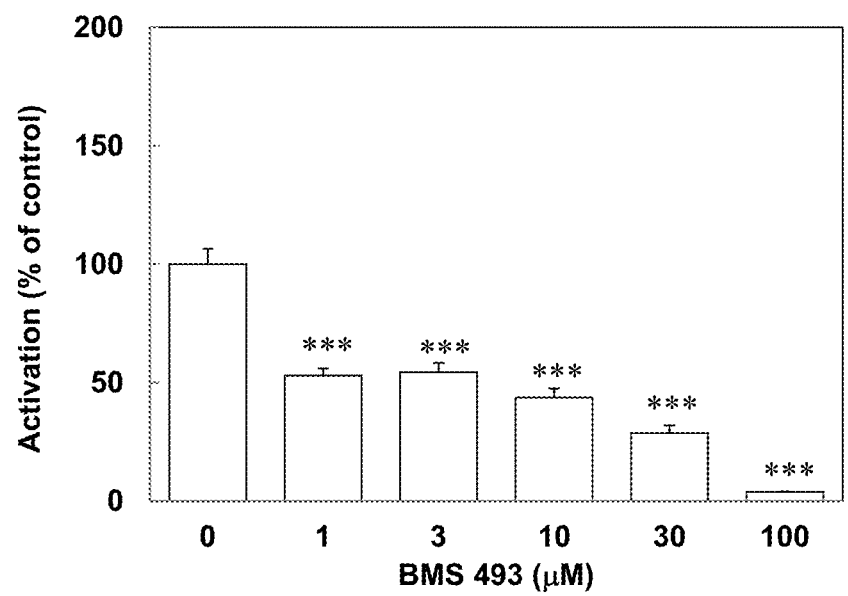

[Figure 6]
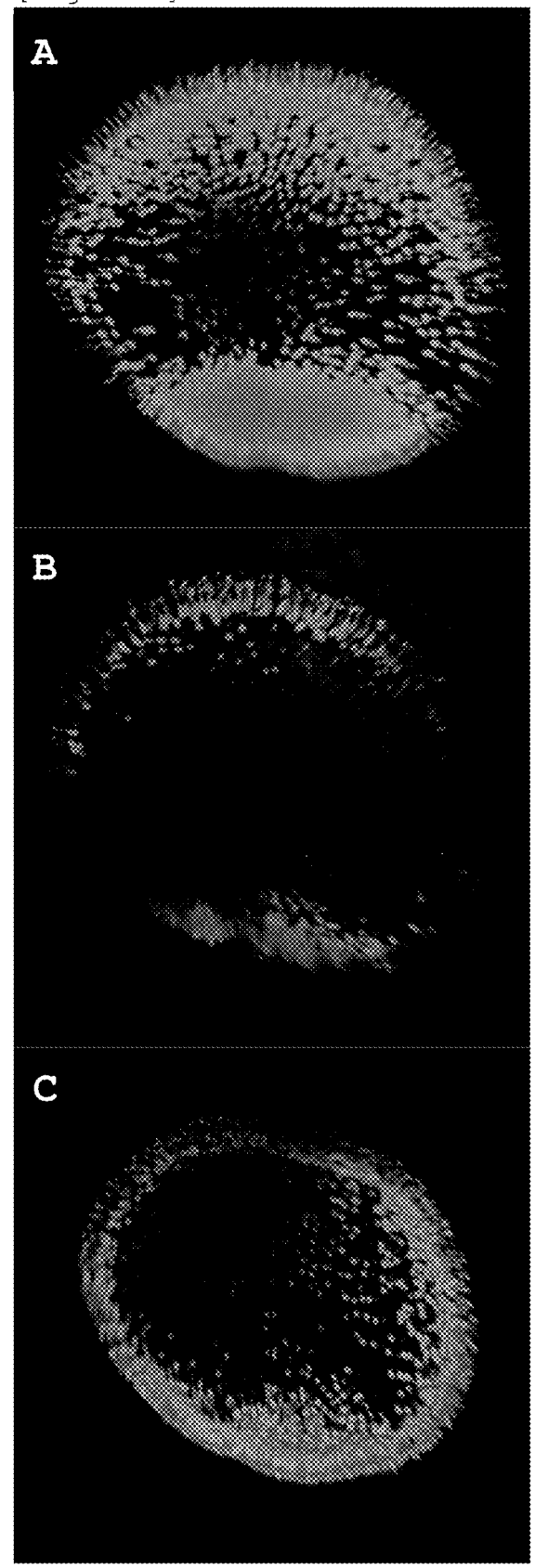

[Figure 7]
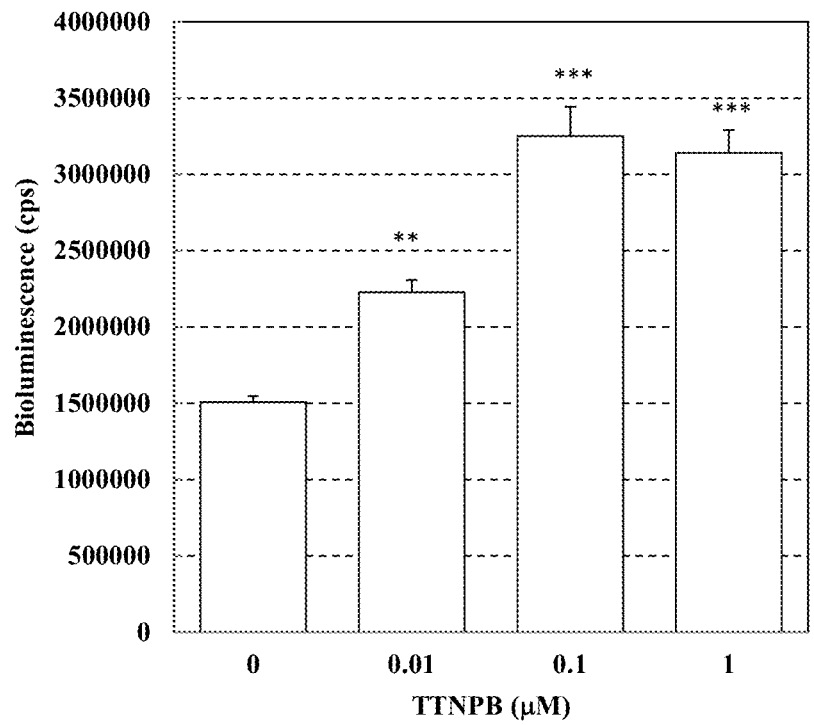
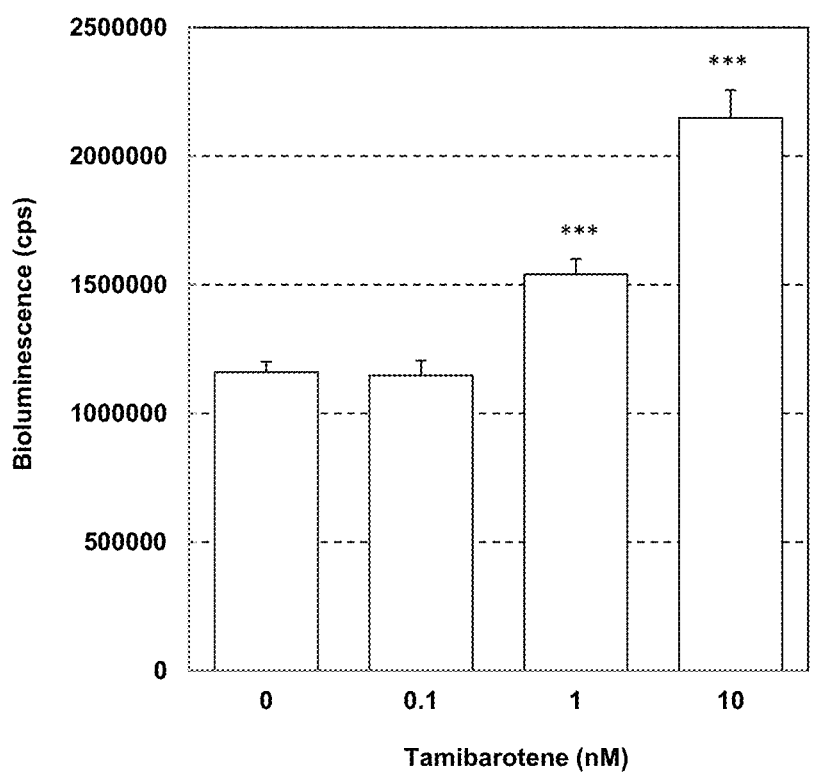

SEQUENCE LISTING

```
<160> NUMBER OF SEQ ID NOS: 7

<210> SEQ ID NO 1
<211> LENGTH: 1873
<212> TYPE: DNA
<213> ORGANISM: Danio rerio

<400> SEQUENCE: 1
gcaaagcaat gtcatttaag tgagctttaa tctagatctt caccattact cacaacatat     60
cacacctaac aatgattaat taactcaata aaagcagcac atattcctgg cagagctcat    120
cagattgaac gctagtgcat agagatcttg tccaatcatg aggccagtgt gtgccaggtt    180
tgctctttct gtttggaagt ggtatcctgt taaacataag atgtttgaaa catgtcaaat    240
ctaaactccc caaatgctgc cgcaaactaa actgatagag aacatgctgc tgtccctgtg    300
ttattgttca gattgtgtga atactgagat tataatgagc aattaggaac atttcccctt    360
tccatcttcc catgcagtgt ggatcgtagt cagactagca agctgctaat gtgcttaagg    420
ctcatggttt tagagtaact ctcctgtaat ccgcaaatcc tcttcataaa acccacctgt    480
gtgaaatatg ctgagccctg agcatccagg cctttcacag ggccaagggt agccgtagtc    540
cccctgactc cacacaatct ggaacatgca cagcttaaaa taagacagac cagatttcta    600
atcactgaat tcttgtgctt caatcagatg cggtgtgtca tctttggctg gttaatcatg    660
ttttttttca gaaatctggt ttctttagcg taggtggtaa tgaactggac tagcatcccc    720
atgaaacgca caacctggct aaaatgttca tcttgagctc tgggatagat ccttctggta    780
tagatctatt atttaacctg ctttattgtt gcaaagcaaa gggcatcggc tgcgtaataa    840
catgctggat aagttgttgg ttcattccgc tgtggcaacc cttgattaat aaagggacta    900
aactaaaaag aaaatgaatg aatgaatgaa tgaaagaatg aatgaatgaa taaatgttcc    960
aaagcagttt gacaaataat cagaacaata acagaattga ttatgtctga aatacgctca   1020
ttctactgtg gcaagtttat attttgacca tatcttagta atttcctgca gttgtctcca   1080
gttatatttt agaataaaat taaaaacttt aaaagacgga ctactctcag agaatgtgtg   1140
ttggacactg aggaaggtcc cgcataagcg aacgcttgta gactttcagc atgcactgag   1200
cactttgtat aaacccaaat caaacaacat tgctagaatc tcgacaagtg aactgtttct   1260
ggacatttgc agatgagctt ctgctttgcc ttctgatgga ttagattatt aatttaacat   1320
agtgttaaag gtgaactcag cacaagatcc tcctctttta catgctgtct ttaattatac   1380
gccacacaga cactctgcag tattcacact ggaccttctg agtcttgatc atggaaaagt   1440
tcgatatcat tttccttttg aaacgcttcc gctttcaatc atttcagcca aacacaactg   1500
```

```
tgatgttgct gtctgtgtgt tggagaactt catagtagaa gtgtgctgtt gtgtgagaga    1560
aagttcttat tatctacctg ctgctcaggt acaaccttaa taagttgata agttgccaga    1620
tatgcagtgc aatgatggct gggattattt tattatctct ggcctaaata gactgctgct    1680
gacagcctgg aaacatcagc taatccccat tgagtctcta taaagcgggg tgtccgatcg    1740
ccccatccag tcgtagcacg gtcctgcctc gtttcttcac agtcctgccc agacatctag    1800
agattaccgc agaaggggct gagcgccaca tccaaccgca gccatgaacg gtacagaggg    1860
accggcattc tac                                                      1873

<210> SEQ ID NO 2
<211> LENGTH: 1769
<212> TYPE: DNA
<213> ORGANISM: Danio rerio

<400> SEQUENCE: 2
aaccacttgt tacaaccaag ctctggaata gagcatatac aacaaatttc ttgaaacaag      60
tgagctacag cagcagcaga agaagagcaa gaatggtgca ctcacactag accctaatta     120
aacacacctg atcttactta ttgagtcctt gaaacctaca ggtgaagcta ggatcacact     180
tgactttttt ccccatggac ttccattcat gcgcccgcaa atgcgtcaga ccacaaacgc     240
agggtcatgc gttaagtttc acaggtcgct gcagtgcaaa gttaagcttg gtaaactct     300 gacctgcgaa atcgcatccc cttttcgcag cgccgtacga cagaatttcg cacacacaaa     360
ctctagtgtg accgcagctt aagtgtgttg aagcagggtt ggaactaaac tgtgcagggt     420
tgcggccctt caggatctaa gtttgacacc ccttgactat ccgaaccatg cacggttcgt     480
ttgacaagta tgagtgctct aaatcaggcc caggtgcggt tcagttggcc ggccatggct     540
tggttggaag aggtgtgcca agctcagtt cggttgggtt ttggcacggt acgcttgtag     600
tgtaagcgca gagcacgtct gtgcccataa tgcctactga ttaatttggc cttgggttca     660
aggcagctgt acctagtgtg tgtacaccct aagaataaga aactgaatct acaatttaca     720
caagatcata attgcagtta gactggacag tagactagaa aaacatttat acactcactt     780
catcgacgtc taataattta ttttatttta tttttaatct cagccctttc tgcagctttg     840
tttcacatgc tcaaacacta gtttgaccaa agcttaaatc agttgtgtta aataagagac     900
attcaaaata aatgtaaatg agctctccaa atcagcagac ttaacattct ttaaaatgat     960
tgattcaata gtgataaaaa tcaggcatag ccagttgtaa ctttagataa attacagaaa    1020
atgtcaaata cagagaaccg attctttttt atgatacatc caagcacaca tttaacacaa    1080
tccaggcaaa ccccgaattt cacagtcaca agcactgttt gtacaagagc tttgcctaag    1140
gacacacagt ctctataagt ccaggtcgtt ggtttcactc ttattttaaa catgtgacat    1200
ttttcctgcc atcctgtctt aggctgctgt ttgcttcatt ccatgtcaca ttaaattcct    1260
cagtagcacc ttttacacac acagccaatc ttttccagaa aattcaattg ctttgaagag    1320
ataatgtgtg aacaaatcca tttagaaaag gaaaattaag aatttgtaaa atcatctgta    1380
aattgttggc attcttctgt atatgaacat cacatcattt acaggtaaag gtctggtcat    1440
taattatatg acaatttact ggtattattt tgtgaaaggg gctattttca atgcgttcat    1500
ccatcctttt catccctcaa atctctcatt cacgtccccc tccccatctg cacactttat    1560 ctcatttttcc accctgctgg aatctgagca cttgtgcagt tatcagggct cctgtattta    1620
ggaggctctg ggtgtccatg taggggacga acagaaacac tgcagacctt tatagaagaa    1680
```

| | | |
|---|---|---|
| caattgataa gagtcctcat acataaagac tccattagta agccagtgac ccaggagccc | 1740 | |
| agaccaacag caaagcagac agtgaacat | 1769 | |

<210> SEQ ID NO 3
<211> LENGTH: 1179
<212> TYPE: DNA
<213> ORGANISM: Artificial
<220> FEATURE:
<223> OTHER INFORMATION: Base sequence of NTR-NanoLuc protein coding region

<400> SEQUENCE: 3

| | |
|---|---|
| atggacatca tcagcgtggc tctgaagaga cacagcacaa aggcatttga tgctagcaag | 60 |
| aagctgacac ctgaacaggc cgagcagatc aagacactgc tccagtacag ccctagcagc | 120 |
| acaaacagcc agccttggca cttcatcgtg gctagcacag aggaaggcaa agctagagtg | 180 |
| gctaagagcg ccgctggcaa ctacgtgttc aacgagagaa agatgctgga tgctagccac | 240 |
| gtggtggtgt tctgtgctaa gaccgccatg gacgatgtgt ggctgaagct ggtggtggat | 300 |
| caggaagatg ctgatggcag attcgctaca cctgaagcta aggctgctaa cgacaagggc | 360 |
| agaaagttct tcgccgacat gcacagaaag gatctgcacg atgatgctga gtggatggcc | 420 |
| aagcaggtgt acctgaacgt gggcaacttc ctgctgggcg tggctgctct gggcctcgat | 480 |
| gctgtgccca tcgaaggctt cgatgctgct atcctggatg ccgagttcgg cctgaaggag | 540 |
| aagggctaca aagcctggt ggtggtgcct gtgggccacc acagcgtgga ggacttcaac | 600 |
| gctacactgc ctaagagcag actgccccag aacatcacac tgacagaggt gggcggggcg | 660 |
| ggccgggtct tcacactcga agatttcgtt ggggactggc gacagacagc cggctacaac | 720 |
| ctggaccaag tccttgaaca gggaggtgtg tccagtttgt ttcagaatct cggggtgtcc | 780 |
| gtaactccga tccaaaggat tgtcctgagc ggtgaaaatg gctgaagat cgacatccat | 840 |
| gtcatcatcc cgtatgaagg tctgagcggc gaccaaatgg ccagatcga aaaatttttt | 900 |
| aaggtggtgt accctgtgga tgatcatcac tttaaggtga tcctgcacta tggcacactg | 960 |
| gtaatcgacg gggttacgcc gaacatgatc gactatttcg gacggccgta tgaaggcatc | 1020 |
| gccgtgttcg acggcaaaaa gatcactgta acagggaccc tgtggaacgg caacaaaatt | 1080 |
| atcgacgagc gcctgatcaa ccccgacggc tccctgctgt tccgagtaac catcaacgga | 1140 |
| gtgaccggct ggcggctgtg cgaacgcatt ctggcgtaa | 1179 |

<210> SEQ ID NO 4
<211> LENGTH: 678
<212> TYPE: DNA
<213> ORGANISM: Artificial
<220> FEATURE:
<223> OTHER INFORMATION: Base sequence of DsRed2 protein coding region

<400> SEQUENCE: 4

| | |
|---|---|
| atggcctcct ccgagaacgt catcaccgag ttcatgcgct tcaaggtgcg catggagggc | 60 |
| accgtgaacg gccacgagtt cgagatcgag ggcgagggcg agggccgccc ctacgagggc | 120 |
| cacaacaccg tgaagctgaa ggtgaccaag ggcggccccc tgcccttcgc ctgggacatc | 180 |
| ctgtcccccc agttccagta cggctccaag gtgtacgtga agcaccccgc cgacatcccc | 240 |
| gactacaaga agctgtcctt ccccgagggc ttcaagtggg agcgcgtgat gaacttcgag | 300 |
| gacggcggcg tggcgaccgt gacccaggac tcctccctgc aggacggctg cttcatctac | 360 |
| aaggtgaagt tcatcggcgt gaacttcccc tccgacggcc ccgtgatgca gaagaagacc | 420 |

| | |
|---|---|
| atgggctggg aggcctccac cgagcgcctg taccccgcg acggcgtgct gaagggcgag | 480 |
| acccacaagg ccctgaagct gaaggacggc ggccactacc tggtggagtt caagtccatc | 540 |
| tacatggcca agaagcccgt gcagctgccc ggctactact acgtggacgc caagctggac | 600 |
| atcacctccc acaacgagga ctacaccatc gtggagcagt acgagcgcac cgagggccgc | 660 |
| caccacctgt tcctgtag | 678 |

<210> SEQ ID NO 5
<211> LENGTH: 1389
<212> TYPE: DNA
<213> ORGANISM: Homo sapiens

<400> SEQUENCE: 5

| | |
|---|---|
| atggccagca acagcagctc ctgcccgaca cctgggggcg ggcacctcaa tgggtacccg | 60 |
| gtgcctccct acgccttctt cttccccccct atgctgggtg gactctcccc gccaggcgct | 120 |
| ctgaccactc tccagcacca gcttccagtt agtggatata gcacccatc cccagccacc | 180 |
| attgagaccc agagcagcag ttctgaagag atagtgccca gccctccctc gccaccccct | 240 |
| ctaccccgca tctacaagcc ttgctttgtc tgtcaggaca gtcctcagg ctaccactat | 300 |
| ggggtcagcg cctgtgaggg ctgcaagggc ttcttccgcc gcagcatcca gaagaacatg | 360 |
| gtgtacacgt gtcaccggga caagaactgc atcatcaaca aggtgacccg gaaccgctgc | 420 |
| cagtactgcc gactgcagaa gtgctttgaa gtgggcatgt ccaaggagtc tgtgagaaac | 480 |
| gaccgaaaca agaagaagaa ggaggtgccc aagcccgagt gctctgagag ctacacgctg | 540 |
| acgccggagg tgggggagct cattgagaag gtgcgcaaag cgcaccagga aaccttccct | 600 |
| gccctctgcc agctgggcaa atacactacg aacaacagct cagaacaacg tgtctctctg | 660 |
| gacattgacc tctgggacaa gttcagtgaa ctctccacca gtgcatcat taagactgtg | 720 |
| gagttcgcca gcagctgcc cggcttcacc accctcacca tcgccgacca gatcacccttc | 780 |
| ctcaaggctg cctgcctgga catcctgatc ctgcggatct gcacgcgta cacgcccgag | 840 |
| caggacacca tgaccttctc ggacgggctg accctgaacc ggacccagat gcacaacgct | 900 |
| ggcttcggcc ccctcaccga cctggtcttt gccttcgcca accagctgct gccccctggag | 960 |
| atggatgatg cggagacggg gctgctcagc gccatctgcc tcatctgcgg agaccgccag | 1020 |
| gacctggagc agccggaccg ggtggacatg ctgcaggagc cgctgctgga ggcgctaaag | 1080 |
| gtctacgtgc ggaagcggag gcccagccgc ccccacatgt tccccaagat gctaatgaag | 1140 |
| attactgacc tgcgaagcat cagcgccaag ggggctgagc gggtgatcac gctgaagatg | 1200 |
| gagatcccgg gctccatgcc gcctctcatc caggaaatgt tggagaactc agagggcctg | 1260 |
| gacactctga gcggacagcc gggggtggg gggcgggacg ggggtggcct ggcccccccg | 1320 |
| ccaggcagct gtagccccag cctcagcccc agctccaaca gaagcagccc ggccacccac | 1380 |
| tccccgtga | 1389 |

<210> SEQ ID NO 6
<211> LENGTH: 1347
<212> TYPE: DNA
<213> ORGANISM: Homo sapiens

<400> SEQUENCE: 6

| | |
|---|---|
| atgtttgact gtatggatgt tctgtcagtg agtcctgggc aaatcctgga tttctacact | 60 |
| gcgagtccgt cttcctgcat gctccaggag aaagctctca agcatgcctt cagtggattg | 120 |
| acccaaaccg aatggcagca tcggcacact gctcaatcaa ttgaaacaca gagcaccagc | 180 |

-continued

| | |
|---|---|
| tctgaggaac tcgtcccaag ccccccatct ccacttcctc ccctcgagt gtacaaaccc | 240 |
| tgcttcgtct gccaggacaa atcatcaggg taccactatg gggtcagcgc ctgtgaggga | 300 |
| tgtaagggct ttttccgcag aagtattcag aagaatatga tttacacttg tcaccgagat | 360 |
| aagaactgtg ttattaataa agtcaccagg aatcgatgcc aatactgtcg actccagaag | 420 |
| tgctttgaag tgggaatgtc caaagaatct gtcaggaatg acaggaacaa gaaaagaag | 480 |
| gagacttcga agcaagaatg cacagagagc tatgaaatga cagctgagtt ggacgatctc | 540 |
| acagagaaga tccgaaaagc tcaccaggaa actttccctt cactctgcca gctgggtaaa | 600 |
| tacaccacga attccagtgc tgaccatcga gtccgactgg acctgggcct ctgggacaaa | 660 |
| ttcagtgaac tggccaccaa gtgcattatt aagatcgtgg agtttgctaa acgtctgcct | 720 |
| ggtttcactg gcttgaccat cgcagaccaa attaccctgc tgaaggccgc ctgcctggac | 780 |
| atcctgattc ttagaatttg caccaggtat accccagaac aagacaccat gactttctca | 840 |
| gacggcctta ccctaaatcg aactcagatg cacaatgctg gatttggtcc tctgactgac | 900 |
| cttgtgttca cctttgccaa ccagctcctg cctttggaaa tggatgacac agaaacaggc | 960 |
| cttctcagtg ccatctgctt aatctgtgga gaccgccagg accttgagga accgacaaaa | 1020 |
| gtagataagc tacaagaacc attgctggaa gcactaaaaa tttatatcag aaaaagacga | 1080 |
| cccagcaagc tcacatgtt tccaaagatc ttaatgaaaa tcacagatct ccgtagcatc | 1140 |
| agtgctaaag gtgcagagcg tgtaattacc ttgaaaatgg aaattcctgg atcaatgcca | 1200 |
| cctctcattc aagaaatgct ggagaattct gaaggacatg aacccttgac cccaagttca | 1260 |
| agtgggaaca cagcagagca cagtcctagc atctcaccca gctcagtgga aaacagtggg | 1320 |
| gtcagtcagt caccactcgt gcaataa | 1347 |

<210> SEQ ID NO 7
<211> LENGTH: 1365
<212> TYPE: DNA
<213> ORGANISM: Homo sapiens

<400> SEQUENCE: 7

| | |
|---|---|
| atggccacca ataaggagcg actctttgcg gctggtgccc tggggcctgg atctggctac | 60 |
| ccaggggcag gtttcccctt cgccttccca ggggcactca gggggtctcc gcctttcgag | 120 |
| atgctgagcc ctagcttccg gggcctgggc cagcctgacc tccccaagga gatggcctct | 180 |
| ctgtcggtgg agacacagag caccagctca gaggagatgg tgcccagctc gccctcgccc | 240 |
| cctccgcctc ctcgggtcta caagccatgc ttcgtgtgca atgacaagtc ctctggctac | 300 |
| cactatgggg tcagctcttg tgaaggctgc aagggcttct ttcgccgaag catccagaag | 360 |
| aacatggtgt acacgtgtca ccgcgacaaa aactgtatca tcaacaaggt gaccaggaat | 420 |
| cgctgccagt actgccggct acagaagtgc ttcgaagtgg gcatgtccaa ggaagctgtg | 480 |
| cgaaatgacc ggaacaagaa gaagaaagag gtgaaggaag aagggtcacc tgacagctat | 540 |
| gagctgagcc ctcagttaga agagctcatc accaaggtca gcaaagccca tcaggagact | 600 |
| ttcccctcgc tctgccagct gggcaagtat accacgaact ccgtgcagag ccaccgcgtg | 660 |
| cagctggatc tggggctgtg gacaagttc agtgagctgg ctaccaagtg catcatcaag | 720 |
| atcgtggagt ttgccaagcg gttgcctggc tttacagggc tcagcattgc tgaccagatc | 780 |
| actctgctca agctgccctg cctagatatc ctgatgctgc gtatctgcac aaggtacacc | 840 |
| ccagagcagg acaccatgac cttctccgac gggctgaccc tgaaccggac ccagatgcac | 900 |

-continued

```
aatgccggct tcgggcccct cacagacctt gtctttgcct ttgctgggca gctcctgccc    960
ctggagatgg atgacaccga gacagggctg ctcagcgcca tctgcctcat ctgcggagac   1020
cgcatggacc tggaggagcc cgaaaaagtg gacaagctgc aggagccact gctggaagcc   1080
ctgaggctgt acgcccggcg ccggcggccc agccagccct acatgttccc aaggatgcta   1140
atgaaaatca ccgacctccg gggcatcagc actaagggag ctgaaagggc cattactctg   1200
aagatggaga ttccaggccc gatgcctccc ttaatccgag agatgctgga gaaccctgaa   1260
atgtttgagg atgactcctc gcagcctggt ccccacccca atgcctctag cgaggatgag   1320
gttcctgggg gccagggcaa aggggggcctg aagtccccag cctga                  1365
```

DRUG FOR RETINAL DEGENERATIVE DISEASE ASSOCIATED WITH PHOTORECEPTOR DEGENERATION

TECHNICAL FIELD

The present invention relates to a therapeutic and/or preventive drug for retinitis pigmentosa, and further, a retinoic acid receptor agonist drug useful as a drug for retinal degenerative disease associated with photoreceptor degeneration, including retinitis pigmentosa.

BACKGROUND ART

Retinitis pigmentosa is a progressive retinal degenerative disease starting from degeneration and loss of rod cells of photoreceptor cells. In retinitis pigmentosa, progressive night blindness, visual field constriction and photophobia due to degeneration of photoreceptors cells, are observed, with the result that vision decreases, leading to blindness. Retinitis pigmentosa is known as a hereditary disease. The number of gene mutations causing retinitis pigmentosa and identified up to present are 3000 or more (Non Patent Literature 1). Of them, rhodopsin gene mutation frequently occurs, and 120 or more mutation sites have been found in humans. As a result of classification of rhodopsin gene mutations, it is proposed that 11 mechanisms underlie the process of losing rod-cells (Non Patent Literature 2). Under these circumstances, it is very difficult to narrow down the target molecules for developing a drug. This is considered as a factor that makes it difficult to develop a therapeutic drug for retinitis pigmentosa. Development of a therapeutic method not directly targeted to a gene has been desired (Non Patent Literature 3).

Currently, there is no established therapeutic drug for treating retinitis pigmentosa; however, based on numerous animal experiments and human clinical trials, the following therapeutic possibilities for retinitis pigmentosa have been considered (Non Patent Literature 1):

a) Survival-rate improvement of rod cells, even though it is small, leads to cone-cell protection b) Rod cells, even though they are defective in function, can support survival of cone cells c) If a small number of cone cells can be kept alive in the macular area, it is possible to keep minimum sight sufficiently to walk for oneself.

For the purpose of protecting rod cells or cone cells based on the aforementioned views, e.g., a neurotrophic factor such as CNTF, valproic acid, vitamin A and docosahexaenoic acid (DHA) have been subjected to clinical trials; however, up until now, a distinguishable medicinal effect has not been reported and no compound has been approved by the FDA.

On the other hand, a subject currently actively studied in nonclinical and clinical stages is regenerative medicine, which is provided by transplanting stem cells or rod cells obtained from the stem cells by induction differentiation. However, regenerative medicine has many problems to be solved, such as immune rejection, a low survival rate of transplanted cells, low implantation rate and biosafety (Non Patent Literature 4).

Recently, as a possibility to overcome problems of regenerative medicine through transplantation, assembling endogenous stem cells by a medicinal agent has been considered. As for the regeneration of the retina by endogenous stem cells, it was confirmed, in studies of retina regeneration using zebrafish undertaken so far, that the ablated retina is regenerated. Based on this, the possibility of regeneration of the retina in mammalian adults has been studied by many researchers in the past few years. From these studies, it has been found that Mueller cells having the nature of stem cells proliferate and migrate to an ablated site in the ablated retina; however, a method of inducing rod cells sufficient in number and function from endogenous stem cells has not been established at all. This is a big issue to be solved (Non Patent Literature 5).

In terms of retinal degenerative diseases associated with photoreceptor degeneration, other than retinitis pigmentosa, age-related macular degeneration and macular dystrophy can be mentioned. Since degeneration of photoreceptor cells including rod cells underlies these diseases, it is expected that these diseases can be treated and/or prevented by supplying rod cells. Accordingly, establishing a method for inducing an increase of endogenous rod cells has an extremely great significance in order to provide a therapy for these diseases.

Age-related macular degeneration is a retinal degenerative disease associated with photoreceptor degeneration. In the disease, an ablation is caused in the macula present at the center of the retina with aging, with the result that defects in vision progress, finally leading to a loss of vision. The disease is subdivided into two types, i.e., an atrophic type and an exudative type. In the atrophic type, the macular tissue shrinks, and the retina is ablated, with the result that, e.g., deterioration of vision gradually proceeds. In contrast, in the exudative type, abnormal blood vessels (choroidal neovascularization) develop from the choroid present outside the retina to ablate the retina. Currently, there is no effective treatment for the atrophic type. For the exudative type, a drug therapy using an angiogenesis inhibitor and a surgical procedure exist; however, normal recovery of eyesight cannot be achieved. Development of an effective treatment is desired.

As the angiogenesis inhibitor for use in the treatment of exudative age-related macular degeneration, antibody drugs (Patent Literature 1) and nucleic acid drugs (Patent Literature 2) are known. In addition, a compound having a retinoic acid receptor (hereinafter sometimes referred to as "RAR") agonistic activity has been reported to have an activity to inhibit mouse choroidal neovascularization (Non Patent Literature 6). However, an effect of inducing an increase of rod cells is not reported in this literature.

Macular dystrophy is a group of retinal degenerative disease associated with photoreceptor degeneration. In this disease group, the macula is ablated due to a hereditary cause, with the result that significant deterioration of vision and visual field abnormality take place. Macular dystrophy is subdivided into, e.g., Stargardt disease, cone-rod dystrophy, Best's disease, X-linked juvenile retinoschisis, occult macular dystrophy and central annular choroidal dystrophy. At present, there are no effective treatments.

CITATION LIST

Patent Literature

Patent Literature 1: International Publication No. WO1998/045331

Patent Literature 2: International Publication No. WO1998/018480

Non Patent Literature

Non Patent Literature 1: Pharmacological approaches to retinitis pigmentosa: A laboratory perspective., Prog Retin Eye Res., 2015; 48: 62-81.

Non Patent Literature 2: "Mechanisms of cell death in rhodopsin retinitis pigmentosa: implications for therapy", TRENDS in Molecular Medicine., 2005; 11: 177-185.

Non Patent Literature 3: Farrar G. J., Kenna P. F., Humphries P., "On the genetics of retinitis pigmentosa and on mutation-independent approaches to therapeutic intervention.", EMBO J., 2002; 21 (5): 857-864.

Non Patent Literature 4: He Y, Zhang Y, Liu X et al., "Recent advances of stem cell therapy for retinitis pigmentosa", Int. J. Mol. Sci., 2014; 15 (8): 14456-14474.

Non Patent Literature 5: Yu H, Vu T. H., Cho K., "Mobilizing endogenous stem cells for retinal repair.", Transl. Res., 2014; 163 (4): 387-398.

Non Patent Literature 6: Kami J, Takahashi H et al., "Retinoic acid receptor agonist Am90 inhibits experimental choroidal neovasucularization", Invest. Ophthalmol. Vis. Sci., 2004; 45: 1856. (ARVO Annual Meeting Abstract, May 2004)

SUMMARY OF INVENTION

Technical Problem

An object of the present invention is to obtain a low-molecular weight compound for simply treating and/or preventing retinitis pigmentosa not by an approach such as gene therapy and regenerative medicine, but by administering a medicine via a conventional route of administration. Another object is directed to a simple treatment and/or prevention of a retinal degenerative disease associated with photoreceptor degeneration.

Solution to Problem

The present inventors have considered that treatment and/or prevention of retinitis pigmentosa can be achieved by inducing regeneration of rod cells, thereby increasing the number of rod cells; and that if the rod-cell regeneration can be induced by a low-molecular weight compound, the compound can be administered in the same dosage form as a conventional drug, and thus, retinitis pigmentosa can be simply treated and/or prevented. However, an evaluation system of rod-cell regeneration induction that could screen many compounds was not available. Then, the present inventors have conducted intensive studies. As a result, they succeeded in preparing a transgenic zebrafish model, the rod cells of which can be specifically ablated and then regeneration thereof can be evaluated by luminescence. Low-molecular weight compounds having a regeneration induction activity were searched by using the model and then screened in-vivo using a rod-cell regeneration evaluation system. As a result, we have found that a compound having a retinoic acid receptor agonistic activity contributes to rod-cell regeneration induction. Further, it has been confirmed that the compound having an RAR agonistic activity induces regeneration of rod cells also in a retinitis pigmentosa disease model.

More specifically, it has been found that regeneration of rod cells can be induced by administration of a compound having an RAR agonistic activity; and that the compound having an RAR agonistic activity is effective for treating and/or preventing retinitis pigmentosa. Based on the findings, the present invention has been accomplished.

Since the compound having an RAR agonistic activity of the present invention has an activity to induce rod-cell regeneration, the compound is effective for treating and/or preventing diseases, the symptom of which is improved by induction of rod-cell regeneration (for example, a retinal degenerative disease associated with photoreceptor degeneration such as retinitis pigmentosa, age-related macular degeneration, macular dystrophy (Stargardt disease, cone-rod dystrophy, Best's disease, X-linked juvenile retinoschisis, occult macular dystrophy and central annular choroidal dystrophy)), as described later.

More specifically, the present invention is concerned with, for example, the following:

[1] An agent for treating and/or preventing retinitis pigmentosa, containing a compound having a retinoic acid receptor agonistic activity or a salt thereof.

[2] The agent for treating and/or preventing retinitis pigmentosa according to [1], wherein the compound having a retinoic acid receptor agonistic activity is a retinoid compound or a retinoid-like agonist compound.

[3] The agent for treating and/or preventing retinitis pigmentosa according to [1], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[4] The agent for treating and/or preventing retinitis pigmentosa according to [1], wherein the compound having a retinoic acid receptor agonistic activity is tamibarotene, tamibarotene methyl ester or tamibarotene ethyl ester.

[5] The agent for treating and/or preventing retinitis pigmentosa according to [1], wherein the compound having a retinoic acid receptor agonistic activity is tamibarotene.

[6] The agent for treating and/or preventing according to any one of [1] to [5], wherein the agent is topically administered to the eye.

[7] A composition for use in treating and/or preventing retinitis pigmentosa containing a compound having a retinoic acid receptor agonistic activity or a salt thereof and a pharmaceutically acceptable formulation component.

[8] The composition according to [7], wherein the compound having a retinoic acid receptor agonistic activity is a retinoid compound or a retinoid-like agonist compound.

[9] The composition according to [7], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[10] The composition according to [7], wherein the compound having a retinoic acid receptor agonistic activity is tamibarotene, tamibarotene methyl ester or tamibarotene ethyl ester.

[11] A compound or a salt thereof having a retinoic acid receptor agonistic activity for use in treating and/or preventing retinitis pigmentosa.

[12] The compound or a salt thereof according to [11], wherein the compound having a retinoic acid receptor agonistic activity is a retinoid compound or a retinoid-like agonist compound.

[13] The compound or a salt thereof according to [11], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[14] The compound or a salt thereof according to [11], wherein the compound having a retinoic acid receptor agonistic activity is tamibarotene, tamibarotene methyl ester or tamibarotene ethyl ester.

[15] Use of a compound having a retinoic acid receptor agonistic activity or a salt thereof for producing a medicament for treating and/or preventing retinitis pigmentosa.

[16] The use according to [15], wherein the compound having a retinoic acid receptor agonistic activity is a retinoid compound or a retinoid-like agonist compound.

[17] The use according to [15], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[18] The use according to [15], wherein the compound having a retinoic acid receptor agonistic activity is tamibarotene, tamibarotene methyl ester or tamibarotene ethyl ester.

[19] A method for treating and/or preventing retinitis pigmentosa, comprising administering a compound having a retinoic acid receptor agonistic activity or a salt thereof.

[20] The method for treating and/or preventing retinitis pigmentosa according to [19], wherein the compound having a retinoic acid receptor agonistic activity is retinoid compound or a retinoid-like agonist compound.

[21] The method for treating and/or preventing retinitis pigmentosa according to [19], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[22] The method for treating and/or preventing retinitis pigmentosa according to [19], wherein the compound having a retinoic acid receptor agonistic activity is tamibarotene, tamibarotene methyl ester or tamibarotene ethyl ester.

[23] A rod-cell regeneration inducer containing a compound having a retinoic acid receptor agonistic activity or a salt thereof.

[24] The rod-cell regeneration inducer according to [23], wherein the compound having a retinoic acid receptor agonistic activity is a retinoid compound or a retinoid-like agonist compound.

[25] The rod-cell regeneration inducer according to [23], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[26] The rod-cell regeneration inducer according to [23], wherein the compound having a retinoic acid receptor agonistic activity is, tamibarotene, tamibarotene methyl ester or tamibarotene ethyl ester.

[27] The rod-cell regeneration inducer according to [23], wherein the compound having a retinoic acid receptor agonistic activity is tamibarotene.

[28] The rod-cell regeneration inducer according to any one of [23] to [27], wherein the rod-cell regeneration inducer is topically administered to the eye.

[29] A composition for use in inducing rod-cell regeneration, containing a compound having a retinoic acid receptor agonistic activity or a salt thereof and a pharmaceutically acceptable formulation component.

[30] The composition according to [29], wherein the compound having a retinoic acid receptor agonistic activity is a retinoid compound or a retinoid-like agonist compound.

[31] The composition according to [29], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[32] The composition according to [29], wherein the compound having a retinoic acid receptor agonistic activity is tamibarotene, tamibarotene methyl ester or tamibarotene ethyl ester.

[33] A compound having a retinoic acid receptor agonistic activity or a salt thereof for use in inducing rod-cell regeneration.

[34] The compound or a salt thereof according to [33], wherein the compound having a retinoic acid receptor agonistic activity is a retinoid compound or a retinoid-like agonist compound.

[35] The compound or a salt thereof according to [33], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[36] The compound or a salt thereof according to [33], wherein the compound having a retinoic acid receptor agonistic activity is tamibarotene, tamibarotene methyl ester or tamibarotene ethyl ester.

[37] Use of a compound having a retinoic acid receptor agonistic activity or a salt thereof for producing a medicament for inducing rod-cell regeneration.

[38] The use according to [37], wherein the compound having a retinoic acid receptor agonistic activity is a retinoid compound or a retinoid-like agonist compound.

[39] The use according to [37], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[40] The use according to [37], wherein the compound having a retinoic acid receptor agonistic activity is tamibarotene, tamibarotene methyl ester or tamibarotene ethyl ester.

[41] A method for inducing rod-cell regeneration, comprising administering a compound having a retinoic acid receptor agonistic activity or a salt thereof.

[42] The method for inducing according to [41], wherein the compound having a retinoic acid receptor agonistic activity is a retinoid compound or a retinoid-like agonist compound.

[43] The method for inducing according to [41], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[44] The method for inducing according to [41], wherein the compound having a retinoic acid receptor agonistic activity is tamibarotene, tamibarotene methyl ester or tamibarotene ethyl ester.

[45] An agent for treating and/or preventing a disease, the symptom of which is improved by induction of rod-cell regeneration, containing a compound having a retinoic acid receptor agonistic activity or a salt thereof.

[46] The agent for treating and/or preventing according to [45], wherein the disease, the symptom of which is improved by induction of rod-cell regeneration, is any one selected from the group consisting of retinitis pigmentosa, age-related macular degeneration, Stargardt disease, cone-rod dystrophy, Best's disease, X linked juvenile retinal segregation, occult macular dystrophy and central annular choroidal dystrophy.

[47] The agent for treating and/or preventing according to [45], wherein the disease, the symptom of which is improved by induction of rod-cell regeneration, is retinitis pigmentosa or age-related macular degeneration.

[48] The agent for treating and/or preventing according to any one of [45] to [47], wherein the compound having a retinoic acid receptor agonistic activity is a retinoid compound or a retinoid-like agonist compound.

[49] The agent for treating and/or preventing according to any one of [45] to [47], wherein the compound having a retinoic acid receptor agonistic activity is tamibarotene, tamibarotene methyl ester, tamibarotene ethyl ester, tazarotene, tazarotenic acid, adapalene, palovarotene, retinol, isotretinoin, alitretinoin, etretinate, acitretin or bexarotene.

[50] The agent for treating and/or preventing according to any one of [45] to [47], wherein the compound having a retinoic acid receptor agonistic activity is tamibarotene, tamibarotene methyl ester or tamibarotene ethyl ester.

[51] The agent for treating and/or preventing according to any one of [45] to [47], wherein the compound having a retinoic acid receptor agonistic activity is tamibarotene.

[52] The agent for treating and/or preventing according to any one of [45] to [51], wherein the agent is topically administered to the eye.

[53] A compound having a retinoic acid receptor agonistic activity or a salt thereof for use in treating and/or preventing a disease, the symptom of which is improved by induction of rod-cell regeneration.

[54] The compound or a salt thereof according to [53], wherein the disease, the symptom of which is improved by induction of rod-cell regeneration, is any one selected from the group consisting of retinitis pigmentosa, age-related macular degeneration, Stargardt disease, cone-rod dystrophy, Best's disease, X linked juvenile retinal segregation, occult macular dystrophy and central annular choroidal dystrophy.

[55] The compound or a salt thereof according to [53], wherein the disease, the symptom of which is improved by induction of rod-cell regeneration, is retinitis pigmentosa or age-related macular degeneration.

[56] Use of a compound having a retinoic acid receptor agonistic activity or a salt thereof for producing an agent for treating and/or preventing a disease, the symptom of which is improved by induction of rod-cell regeneration.

[57] The use according to [56], wherein the disease, the symptom of which is improved by induction of rod-cell regeneration, is any one selected from the group consisting of retinitis pigmentosa, age-related macular degeneration, Stargardt disease, cone-rod dystrophy, Best's disease, X linked juvenile retinal segregation, occult macular dystrophy and central annular choroidal dystrophy.

[58] The use according to [56], wherein the disease, the symptom of which is improved by induction of rod-cell regeneration, is retinitis pigmentosa or age-related macular degeneration.

[59] A method for treating and/or preventing a disease, the symptom of which is improved by induction of rod-cell regeneration, comprising administering a compound having a retinoic acid receptor agonistic activity or a salt thereof.

[60] The method for treating and/or preventing according to [59], wherein the disease, the symptom of which is improved by induction of rod-cell regeneration, is any one selected from the group consisting of retinitis pigmentosa, age-related macular degeneration, Stargardt disease, cone-rod dystrophy, Best's disease, X linked juvenile retinal segregation, occult macular dystrophy and central annular choroidal dystrophy.

[61] The method for treating and/or preventing according to [59], wherein the disease, the symptom of which is improved by induction of rod-cell regeneration, is retinitis pigmentosa or age-related macular degeneration.

[62] A method for producing a retinal tissue, comprising adding a compound having a retinoic acid receptor agonistic activity or a salt thereof to cultured stem cells.

[63] A method for producing a retinal tissue for regenerative medicine, comprising adding a compound having a retinoic acid receptor agonistic activity or a salt thereof to cultured stem cells.

[64] Transgenic zebrafish Tg (rho: NTR-NanoLuc, my17: DsRed2).

[65] A method for screening an agent for treating and/or preventing retinitis pigmentosa using transgenic zebrafish Tg (rho: NTR-NanoLuc, my17: DsRed2).

[66] A method for screening an inducer for rod-cell regeneration using transgenic zebrafish Tg (rho: NTR-NanoLuc, my17: DsRed2).

[67] Plasmid pcDNA3.1-rho-ntr-nanoluc-my17-dsred2.

Other embodiments of the present invention are as follows:

(1a) An agent for treating and/or preventing retinitis pigmentosa containing a compound having a retinoic acid receptor agonistic activity or a salt thereof.

(2a) The agent for treating and/or preventing retinitis pigmentosa according to (1a), wherein the compound having a retinoic acid receptor agonistic activity is a retinoid compound or a retinoid-like agonist compound.

(3a) The agent for treating and/or preventing retinitis pigmentosa according to (1a), wherein the compound having a retinoic acid receptor agonistic activity is tamibarotene, tamibarotene methyl ester, tazarotene, tazarotenic acid, adapalene, palovarotene, retinol, isotretinoin, alitretinoin, etretinate, acitretin or bexarotene.

(4a) The agent for treating and/or preventing retinitis pigmentosa according to (1a), wherein the compound having a retinoic acid receptor agonistic activity is tamibarotene or tamibarotene methyl ester.

(5a) A composition for use in treating and/or preventing retinitis pigmentosa containing a compound having a retinoic acid receptor agonistic activity or a salt thereof and a pharmaceutically acceptable formulation component.

(6a) A compound having a retinoic acid receptor agonistic activity or a salt thereof for use in treating and/or preventing retinitis pigmentosa.

(7a) Use of a compound having a retinoic acid receptor agonistic activity or a salt thereof for producing a medicament for treating and/or preventing retinitis pigmentosa.

(8a) A method for treating and/or preventing retinitis pigmentosa, comprising administering a compound having a retinoic acid receptor agonistic activity or a salt thereof.

(9a) A rod-cell regeneration inducer containing a compound having a retinoic acid receptor agonistic activity or a salt thereof.

(10a) A composition for inducing rod-cell regeneration, containing a compound having a retinoic acid receptor agonistic activity or a salt thereof and a pharmaceutically acceptable formulation component.

(11a) A compound having a retinoic acid receptor agonistic activity or a salt thereof for use in inducing rod-cell regeneration.

(12a) Use of a compound having a retinoic acid receptor agonistic activity or a salt thereof for producing a medicament for inducing rod-cell regeneration.

(13a) A method for inducing rod-cell regeneration, comprising administering a compound having a retinoic acid receptor agonistic activity or a salt thereof.

(14a) An agent for treating and/or preventing a disease, the symptom of which is improved by induction of rod-cell regeneration, containing a compound having a retinoic acid receptor agonistic activity or a salt thereof.

(15a) A compound having a retinoic acid receptor agonistic activity or a salt thereof for use in treating and/or preventing a disease, the symptom of which is improved by induction of rod-cell regeneration.

(16a) Use of a compound having a retinoic acid receptor agonistic activity or a salt thereof for producing an agent for treating and/or preventing a disease, the symptom of which is improved by induction of rod-cell regeneration.

(17a) A method for treating and/or preventing a disease, the symptom of which is improved by induction of rod-cell regeneration, comprising administering a compound having a retinoic acid receptor agonistic activity or a salt thereof.

(18a) A method for producing a retinal tissue, comprising adding a compound having a retinoic acid receptor agonistic activity or a salt thereof to cultured stem cells.

(19a) A method for producing a retinal tissue for regenerative medicine, comprising adding a compound having a retinoic acid receptor agonistic activity or a salt thereof to cultured stem cells.

(20a) Transgenic zebrafish Tg (rho: NTR-NanoLuc, my17: DsRed2).

(21a) A method for screening an agent for treating and/or preventing retinitis pigmentosa using transgenic zebrafish Tg (rho: NTR-NanoLuc, my17: DsRed2).

(22a) A method for screening an inducer for rod-cell regeneration using transgenic zebrafish Tg (rho: NTR-NanoLuc, my17: DsRed2).

Advantageous Effects of Invention

According to the present invention, the number of rod cells can be increased by inducing regeneration of the rod cells by administering a compound having a retinoic acid receptor agonistic activity, and retinitis pigmentosa can be simply treated and/or prevented.

Furthermore, a disease, the symptom of which is improved by induction of rod cell regeneration, can be treated and/or prevented by administering a compound having a retinoic acid receptor agonistic activity according to the present invention.

Moreover, an agent for treating or preventing retinitis pigmentosa can be screened using transgenic zebrafish according to the present invention and a method for screening an inducer for rod-cell regeneration using the zebrafish.

BRIEF DESCRIPTION OF DRAWINGS

FIG. 1 shows that, in eyeballs of transgenic zebrafish, Tg (rho: NTR-NanoLuc, my17: DsRed2), produced in Example 2, specific expression of ntr-nanoluc gene was confirmed in the outer granule layer in which rod cells are present, by in-situ hybridization. Reference symbol, AS, represents expression of the ntr-nanoluc gene by an antisense RNA probe, and white arrows point out positive signals. Reference symbol, S, represents background by a sense RNA probe.

FIG. 2 shows that rod cells of transgenic zebrafish Tg (rho: NTR-NanoLuc, my17: DsRed2) produced in Example 2 were ablated by treating the fish with 10 mM metronidazole (MTZ) for 24 hours and the number of rod cells was reduced to 13.5% by cell death. The vertical axis represents the amount of luminescence. Symbol * shows $p<0.001$ in Student t test.

FIG. 3 shows that gradual regeneration of rod cells was confirmed in 48 hours by washing transgenic zebrafish Tg (rho: NTR-NanoLuc, my17: DsRed2) produced in Example 2 and having rod cells ablated with rearing water to remove a toxic radical. The vertical axis represents the amount of luminescence and the horizontal axis represents time after removal of the radical.

FIG. 4 shows the results of a reproducibility test and a concentration-dependence test in relation to rod-cell regeneration with TTNPB in Example 3. The vertical axis represents Activation, which was calculated based on an increase of the amount of luminescence and serves as an index of rod-cell regeneration inducing activity. Symbol * represents $p<0.05$ in the Dunnett multiple comparison test and symbol ** represents $p<0.01$ in the Dunnett multiple comparison test.

FIG. 5 shows the effects (verification results) of an RAR agonist, compound (RA), and an RAR antagonist, compound (BMS493) on induction of rod-cell regeneration according to Example 4. The vertical axis represents Activation, which was calculated based on an increase of the amount of luminescence and serves as an index of rod-cell regeneration inducing activity. Symbol *** represents $p<0.001$ in the Dunnett multiple comparison test.

FIG. 6 shows the state of the rod-cell regeneration effect in the retinitis pigmentosa model of Example 7. The state of the fish obtained by crossing zebrafish Tg (rho: EGFP) specifically expressing EGFP in rod cells (control) with wild-type zebrafish is shown in (A); and the state of the fish obtained by crossing zebrafish Tg (rho: EGFP) with retinitis pigmentosa model zebrafish and not treated with a drug is shown in (B). Loss of rod cells was observed in (B) in comparison with (A). Recovery of rod cells was observed in (C) using the same model administered with TTNPB in comparison with the fish (B) not treated with a drug.

FIG. 7 shows that the rod-cell regeneration induction activity by administration of TTNPB and tamibarotene to the retinitis pigmentosa model according to Example 8 increases in a concentration-dependent manner. The vertical axis represents the amount of luminescence. Symbol  represents $p<0.01$ in the Dunnett multiple comparison test and symbol * represents $p<0.001$ in the Dunnett multiple comparison test.

DESCRIPTION OF EMBODIMENTS

Now, preferred embodiments for carrying out the present invention will be described, below.

The present invention relates to treatment and/or prevention of a disease including retinitis pigmentosa (hereinafter referred to as "retinitis pigmentosa, etc."), the symptom of which is improved by inducing rod cell regeneration based on increasing the number of rod cells by inducing rod cell regeneration by a compound. More specifically, the present invention relates to treatment and/or prevention for retinitis pigmentosa, etc. by regenerating rod cells once degenerated/lost by inducing the regeneration of rod cells by administering a compound having a retinoic acid receptor agonistic activity to increase the number of rod cells.

First, the present inventors constructed a model for evaluating induction of rod cell regeneration. More specifically, transgenic zebrafish Tg (rho: NTR-NanoLuc, my17: DsRed2) were prepared by introducing plasmid pcDNA3.1-rho-ntr-nanoluc-my17-dsred2 in accordance with a gene introduction method using I-SceI meganuclease (Examples 1 and 2). Transgenic zebrafish Tg (rho: NTR-NanoLuc, my17: DsRed2), in which a fluorescent protein, DsRed2, which is cardiac-tissue specifically expressed by cardiomyocyte-specific my17 promoter, can be simply detected by using dsRed2 as a marker under a fluorescence stereomicroscope. In the transgenic zebrafish, in addition to cardiac tissue specific expression of DsRed2, a reductase, i.e., nitroreductase (NTR), and a photoprotein, i.e., NanoLuc fusion protein (NTR-NanoLuc), are expressed by a rod-cell specific rho promoter, in a rod-cell specific manner. NTR-NanoLuc expressed only in rod cells does not affect the general health of the fish under general rearing conditions. However, if, a prodrug, metronidazole, is added, non-toxic metronidazole is converted to a toxic radical by NTR. In this mechanism, by exposing the transgenic zebrafish to metronidazole, ablation is specifically directed to the rod cells without affecting the general health of the fish. After rod cells are ablated by treatment with metronidazole, the transgenic zebrafish were washed with rearing water to remove the toxic radical. Thereafter, rod-cells are gradually regenerated in the zebrafish. In the transgenic zebrafish, rod cells can be quantitatively determined by measuring the amount of luminescence derived from rod-cell-specific NanoLuc expression. After the rod cells are ablated, the transgenic zebrafish are exposed to a test compound. The activity of the test compound to induce rod-cell regeneration can be quantitatively evaluated by measuring the amount of luminescence derived from NanoLuc and specific to rod cells.

Juvenile zebrafish can be raised in, e.g., a 96-well plate. By virtue of using transgenic zebrafish Tg (rho: NTR-NanoLuc, my17: DsRed2), a method for quantitatively screening a compound having a rod regeneration induction activity in the 96-well plate with high throughput was established. This evaluation system is a first screening method that enables quantitative evaluation of tissue regeneration in-vivo with high throughput.

Validation of the transgenic zebrafish was carried out by several methods. First, in-situ hybridization was carried out. As a result, it was confirmed that ntr-nanoluc was specifically expressed in the outer granule layer in which rod cells are present (FIG. 1). Then, the transgenic zebrafish was treated with 10 mM metronidazole for 24 hours. As a result, it was confirmed that rod cells were ablated, and the number of rod cells reduced to 13.5% by cell death (FIG. 2). After giving ablation, the transgenic zebrafish were washed with rearing water to remove a toxic radical derived from metronidazole. As a result, it was confirmed that rod cells are gradually regenerated over 48 hours (FIG. 3). At this stage, if a test compound is added, the rod-cell regeneration induction activity of the compound can be confirmed.

Luminescence from transgenic zebrafish Tg (rho: NTR-NanoLuc, my17: DsRed2), even from a single individual, can be sufficiently detected. In the screening using transgenic zebrafish according to the present invention, if 4 or more samples are used in screening and a concentration dependence test is further carried out in combination, the rod-cell regeneration induction activity can be more certainly confirmed.

As a result of screening using transgenic zebrafish, the present inventors found that 4-[(E)-2-(5,6,7,8-tetrahydro-5,5,8,8-tetramethyl-2-naphthalenyl)-1-propenyl]benzoic acid (TTNPB) is effective in inducing regeneration of rod cells, thereby increasing the number of rod cells. We have confirmed that TTNPB showed a statistically significant rod-cell regeneration induction activity compared to DMSO control at any predetermined concentration in a concentration dependence test. Note that it was determined that the medicinal effect of TTNPB already reached the saturation point even at a concentration of 0.3 µM, and thus, TTNPB is determined to be a compound having a high activity (Example 3: FIG. 4). TTNPB is known to be a retinoic acid receptor (RAR) agonist. More specifically, since TTNPB was confirmed to have a rod-cell regeneration induction activity, relevance of rod-cell regeneration induction to a retinoic acid signal was presumed.

Based on this finding, an endogenous agonist of a retinoic acid signal, i.e., All-trans retinoic acid, was evaluated. As a result, All-trans retinoic acid exhibited a significant regeneration induction activity in a concentration dependent manner. From this, the relevance of rod-cell regeneration induction to a retinoic acid signal became clear (Example 4: FIG. 5). Further, 4-[(1E)-2-[5,6-dihydro-5,5-dimethyl-8-(2-phenylethynyl)-2naphthalenyl]ethenyl]benzoate (BMS493), known as an RAR antagonist inhibiting RAR, does not show rod-cell regeneration induction activity and was lower than a DMSO control. From this, it was considered that the RAR antagonist inhibits naturally occurring rod-cell regeneration in the presence of an RAR agonist. From the above results, it was suggested that activation of retinoic acid signal via RAR contributes to rod-cell regeneration induction (Example 4: FIG. 5).

Next, the RAR agonistic activity was examined for tamibarotene, tamibarotene methyl ester, tamibarotene ethyl ester, adapalene, tazarotene, tazarotenic acid and palovarotene. As a result, it was confirmed that all of the compounds have RARα, RARβ and RARγ agonist activities (Table 2).

These compounds, which were used as representative examples of RAR agonists, were subjected to evaluation of rod-cell regeneration induction activity. As a result, it was confirmed that all of the compounds exhibit rod-cell regeneration induction activity in a concentration dependent manner (Example 6; Table 3). Of these RAR agonists, tamibarotene and tamibarotene ethyl ester exhibited a strong rod-cell regeneration induction activity.

Transgenic zebrafish Tg (rho: hRHO (Q344X), omp: EGFP), known as a retinitis pigmentosa pathological model, were crossed with transgenic zebrafish Tg (rho: NTR-NanoLuc, my17: DsRed2) prepared by the present inventors. In this manner, a new pathological model having the property of emitting light from regenerated rod cells was prepared to realize quantitative evaluation for rod-cell regeneration. Transgenic zebrafish Tg ((rho: hRHO (Q344X), omp: EGFP), which is a name under another nomenclature system of a retinitis pigmentosa model, i.e., zebrafish RH1: hRhodopsin (Q344X) (Nakao T, Tsujikawa M, Notomi S, Ikeda Y, Nishida K., "The role of mislocalized phototransduction in photoreceptor cell death of retinitis pigmentosa.", PLoS One., 2012; 7 (4): e32472)), can express a rhodopsin mutant, hRHO (Q344X), which was reported as a causal gene mutation of retinitis pigmentosa in humans, in a rod-cell specific manner; are confirmed to exhibit ectopic expression of rhodopsin and degeneration/loss of rod cells; and have an identical phenotype with that of human retinitis pigmentosa.

Using the new pathological model zebrafish, the rod-cell regeneration induction activity of RAR agonists, i.e., TTNPB and tamibarotene, was quantitatively evaluated. As a result, it was confirmed that both TTNPB and tamibarotene induce statistically significant rod cell regeneration in a dose-dependent manner (Example 8, FIG. 7).

Using Tg (rho: EGFP) specifically expressing EGFP (enhanced green fluorescent protein) in rod cells, the state of rod cells in a retinitis pigmentosa model was observed by a confocal laser microscope. As a result, it was found that the number of rod cells was apparently reduced in the retinitis pigmentosa model compared to a wild type. In contrast, in the group treated with TTNPB, it was found that the number of rod cells recovered compared to the control (Example 7, FIG. 6).

As confirmed by verification using zebrafish as mentioned above, a compound having an RAR agonistic activity can induce regeneration of rod cells and can treat and/or prevent retinitis pigmentosa, etc.

For treatment and/or prevention of retinitis pigmentosa, etc., which is an object of the present invention, a compound having a retinoic acid receptor agonistic activity (RAR agonistic activity) may be used. In the present invention, the compound having a retinoic acid receptor agonistic activity refers to a compound that can bind to a retinoic acid receptor (RAR) to activate it. Examples of such a compound include a retinoid compound and a retinoid-like agonist compound. The retinoid compound refers to a natural retinoid or synthetic retinoid. The natural retinoid collectively represents vitamin A and vitamin A derivatives. Examples thereof include retinoic acid, retinol, retinal and 3-dehydro derivatives of these. The synthetic retinoid refers to a compound synthetically obtained from a retinoid and having an RAR agonistic activity. A retinoid-like agonist compound is a compound having an RAR agonistic activity, although it does not have the structure of vitamin A. Whether or not a compound has an RAR agonistic activity can be determined, for example, by the RAR agonistic activity measurement method described later in Example 5.

Examples of the compound having an RAR agonistic activity of the present invention include tamibarotene (for example, Combi-Blocks, Cat. No. QA-6963), tamibarotene methyl ester (for example, Sundia meditech, Cat. No. 82569), tamibarotene ethyl ester (synthesized by the method described for example, in Org. Lett., 15, 3678-3681 (2013)), tazarotene (for example, Tokyo Kasei, Cat. No. T3108), tazarotenic acid (obtained, for example, by hydrolysis of tazarotene with reference to the method described in U.S. Pat. No. 6,344,463), adapalene (for example, Tokyo Kasei, Cat. No. A2549), palovarotene (for example, Haoyuan Chemexpress Co., Ltd., Cat. No. HY-14799), retinol (for example, Sigma-Aldrich, Cat. No. R7632-25MG), isotretinoin (for example, Sigma-Aldrich, Cat. No. 1353500-200MG), alitretinoin, etretinate (for example, Sigma-Aldrich, Cat. No. 1011029-20MG), acitretin (for example, Sigma-Aldrich, Cat. No. 44707-25MG), bexarotene (for example, Sigma-Aldrich, Cat. No. S ML0282-10MG) and TTNPB (Sigma-Aldrich, Cat. No. T3757-10MG). Preferably, tamibarotene, tamibarotene methyl ester or tamibarotene ethyl ester is mentioned; and further preferably, tamibarotene is mentioned.

The compound having an RAR agonistic activity to be used in the present invention, if desired, can be used in the form of a pharmaceutically acceptable salt. The pharmaceutically acceptable salt refers to a salt having no significant toxicity and usable as a medicine. Compounds having an RAR agonistic activity to be used in the present invention sometimes have an acid moiety, particularly, a carboxy group. Accordingly, the compounds are treated with a base to obtain salts thereof.

Examples of salts based on acidic substituents include an alkali metal salt such as a sodium salt, a potassium salt and a lithium salt; an alkaline earth metal salt such as a calcium salt and a magnesium salt; a metal salt such as an aluminum salt and an iron salt; an inorganic salt such as an ammonium salt; an organic amine salt such as a t-octylamine salt, a dibenzylamine salt, a morpholine salt, a glucosamine salt, a phenylglycine alkyl ester salt, an ethylenediamine salt, a N-methyl glucamine salt, a guanidine salt, a diethylamine salt, a triethylamine salt, a dicyclohexylamine salt, N,N'-dibenzylethylenediamine salt, a chloroprocaine salt, a procaine salt, a diethanolamine salt, N-benzyl-phenethylamine salt, a piperazine salt, a tetramethylammonium salt and a tris(hydroxymethyl)aminomethane salt; and an amino acid salt such as a glycine salt, a lysine salt, an arginine salt, an ornithine salt, a glutamate and an aspartate.

A compound having an RAR agonistic activity or a salt thereof to be used in the present invention sometimes absorbs and adsorbs water and is converted into a hydrate when it is left in the air or recrystallized. Such a hydrate is also included in the compound or a salt thereof of the present invention.

A compound having an RAR agonistic activity or a salt thereof to be used in the present invention sometimes absorbs a solvent and is converted into a solvate. Such a solvate is also included in the compound or a salt thereof of the present invention.

The solvent that can form a solvate is not particularly limited as long as it does not exhibit significant toxicity and can be used as a medicine. Examples of the solvent include ethanol, 1-propanol, 2-propanol, 1-butanol, 2-butanol, acetone, methyl ethyl ketone, methyl isobutyl ketone, dimethyl sulfoxide, ethyl formate, ethyl acetate, propyl acetate, diethyl ether, tetrahydrofuran, formic acid, acetic acid, pentane, heptane, cumene and anisole.

If a compound having an RAR agonistic activity to be used in the present invention has an asymmetric carbon atom within the molecule, optical isomers are present. These isomers and mixtures of these isomers can be used for attaining an object of the present invention. Accordingly, the compounds having an RAR agonistic activity to be used in the present invention, single optical isomers, and mixtures of optical isomers containing them in any ratio are all included within the scope of the present invention.

The optical isomers mentioned above can be obtained by synthesizing a compound according to the present invention by using an optically active starting compound or using asymmetric synthesis or an asymmetric induction method. Alternatively, an optical isomer can be isolated by subjecting synthesized compounds according to the present invention to e.g., optical resolution or separation using an optically active carrier.

A compound having an RAR agonistic activity to be used in the present invention may contain an isotope of at least one constituent atom in a non-natural proportion. As the atomic isotope, e.g., deuterium ($^2$H), tritium ($^3$H), iodine-125 ($^{125}$I), or carbon-14 ($^{14}$C) can be mentioned. The compound can be labeled with a radioisotope such as tritium ($^3$H), iodine-125 ($^{125}$I) or carbon-14 ($^{14}$C). The radiolabeled compounds are useful as therapeutic agents or preventive agents and as reagents such as an assay reagent and a diagnostic agent, for example, an in-vivo diagnostic imaging agent. All isotope variants of the compound of the present invention are included in the scope of the present invention whether it is radiolabeled or not.

The compound having a retinoic acid receptor agonistic activity according to the present invention, since it has an activity to induce rod-cell regeneration, is expected to have an excellent therapeutic effect and/or a preventive effect on diseases, the symptoms of which are improved by the activity, such as retinitis pigmentosa, age-related macular degeneration, macular dystrophy (Stargardt disease, cone-rod dystrophy, Best's disease, X linked juvenile retinal segregation, occult macular dystrophy and central annular choroidal dystrophy) or on symptoms associated with these diseases. The primary pathologic condition of these diseases is known to be degeneration of photoreceptor cells including rod cells (see, for example, the following literature: retinitis pigmentosa (A, E), age-related macular degeneration (B), Stargardt disease (C, E), cone-rod dystrophy (E), Best's disease (D, E), X linked juvenile retinal segregation (E), occult macular dystrophy (F), central annular choroidal dystrophy (G)). On the other hand, it has been elucidated that the disease state caused by degeneration of photoreceptor cells can be improved by supply of rod cells by transplantation (X). Thus, according to the present invention, endogenous rod-cell regeneration is induced by administering a compound having a retinoic acid receptor agonistic activity, thereby increasing the number of rod cells. Thus, the present invention is effective in the treatment and/or prevention of diseases having photoreceptor degeneration (preferably, the diseases mentioned above).

A, Exp Eye Res. 2016 September; 150: 149-165.
B, Am J Ophthalmol. 2016 August; 168: 260-268.
C, Biochim Biophys Acta-Mol Cell Biol Lipid. 2009 Jul; 1791 (7): 573-583.
D, Prog Retin Eye Res. 2017 May; 58: 70-88.
E, Dev Ophthalmol. 2014; 53: 44-52.
F, Jpn J Ophthalmol. 2015 March; 59 (2): 71-80.
G, J Optom. 2013 April; 6 (2): 114-122.
X, Nature. 2006 November 9; 444 (7116): 203-207.

In the present invention, the age-related macular degeneration is defined to include both an atrophic type and an exudative type of age-related macular degeneration, and preferably the atrophic type of age-related macular degeneration.

The compound having a retinoic acid receptor agonistic activity according to the present invention, since it has a rod-cell regeneration induction activity, is effective in the treatment and/or prevention of both the atrophic type and exudative type (preferably, atrophic type) of age-related macular degeneration.

The macular dystrophy in the present invention refers to a group of retinal degenerative diseases having macular damage associated with photoreceptor degeneration due to a hereditary cause and a progression of deterioration of vision/visual field abnormalities; and more specifically, refers to Stargardt disease, cone-rod dystrophy, Best's disease, X linked juvenile retinal segregation, occult macular dystrophy and central annular choroidal dystrophy.

The treatment in the present invention refers to a treatment to be applied to the retina which loses function due to the degeneration or loss of rod cells in order to recover visual function. For the recovery, for example, it is necessary to increase the number of rod cells or induce an increase of rod cells and further protect rod cells from losing function. The compound having a retinoic acid receptor agonistic activity can be suitably applied to this purpose.

The prevention of the present invention refers to eliminating a risk of onset of retinitis pigmentosa, etc. by facilitating or inducing regeneration of rod cells and further preventing functional loss of rod cells in the conditions where degeneration and loss of rod cells proceeds with a high probability and the risk of onset of retinitis pigmentosa, etc. becomes high. For the prevention, the compound having a retinoic acid receptor agonistic activity can be suitably applied.

The mechanism underlying both the treatment and prevention for retinitis pigmentosa, etc. is to induce rod-cell regeneration by administering a compound having a retinoic acid receptor agonistic activity.

The compound of the present invention, a pharmaceutically acceptable salt, a hydrate or a solvate thereof can be administered in various dosage forms. The dosage form is preferably a dosage form topically administered to the eye. For the topical administration to the eye, e.g., a fluid (for example, ophthalmic solution and injection) and an ointment can be used.

In the case of the fluid, a liquid, an emulsion or a suspension can be used. The liquid, emulsion or suspension is preferably sterilized and adjusted to be isotonic to blood. The solvent for use in production of the liquid, emulsion or suspension is not particularly limited as long as it can be used as a diluent for medical use. Examples of the solvent include water, ethanol, propylene glycol, ethoxylated isostearyl alcohol, polyoxylated isostearyl alcohol and polyoxyethylene sorbitan fatty acid ester. Note that, in this case, a sufficient amount of salt, glucose or glycerin to prepare an isotonic solution may be contained in the preparation, as well as a solubilizer, a buffer and a soothing agent usually used. An ophthalmic solution can be prepared, for example, by using additives selected, as appropriate, from a tonicity agent such as sodium chloride and concentrated glycerin; a pH regulator such as hydrochloric acid and sodium hydroxide; a buffering agent such as sodium phosphate and sodium acetate; a surfactant such as polyoxyethylene sorbitan monooleate, polyoxyl stearate 40 and polyoxyethylene hydrogenated castor oil; a stabilizer such as sodium citrate and sodium edetate; and a preservative such as benzalkonium chloride and paraben. The pH of the ophthalmic solution may be sufficient to fall within the acceptable range of ophthalmic preparations, and preferably falls within the range of 4 to 8.

The ointment can be prepared by using an ointment base for an eye ointment and an aid such as liquid paraffin. In the preparation mentioned above, if necessary, e.g., a colorant and a preservative, may be contained, and further, another medicine can be contained.

The content of a compound serving as an active ingredient in the preparation mentioned above is not particularly limited and may be appropriately selected from a wide range. The content usually falls within the range of 0.5 to 70 wt % and preferably 1 to 30 wt %.

The use amount thereof varies depending on the symptom and age of the patient (warm-blooded animal, particularly human). In the case of a liquid eye drop or an intravitreal injection, the upper limit of the use amount per day per eye is 10 mg (preferably 1 mg) and the lower limit thereof is 0.001 mg (preferably 0.01 mg). The use amount (dosage amount) is desirably administered in a single-dose to 6-dose packages per adult per day depending on the symptom. The dosage amount and dose regimen are applicable to eye ointments.

A retinal tissue such as a sheet-like, organoid-like and suspension-like retinal tissue can be effectively produced, in vitro, by adding a compound having a retinoic acid receptor agonistic activity to cultured stem cells such as embryonic stem cells, adult stem cells and induced pluripotent stem cells. The retinal tissue produced ex vivo as mentioned above can be subjected to regenerative medicine by transplanting it in the eyeball.

EXAMPLES

The present invention will be more specifically described by way of Examples shown below; however, the present invention is not limited to these.

Example 1

Preparation of Plasmid pcDNA3.1-rho-ntr-nanoluc-my17-dsred2

To prepare transgenic zebrafish Tg (rho: NTR-NanoLuc, my17: DsRed2), first, plasmid pcDNA3.1-rho-ntr-nanoluc-my17-dsred2 was prepared using an In-Fusion (registered trademark) HD Cloning Kit. A method for forming a vector was carried out in accordance with the manual attached to the kit. The nucleotide sequences introduced herein are shown in SEQ ID NOs: 1 to 4.

Example 2

Preparation of Transgenic Zebrafish Tg (rho: NTR-NanoLuc, my17: DsRed2) and Validation of Evaluation of Rod-Cell Regeneration Induction

[Preparation of Transgenic Zebrafish]
Using plasmid pcDNA3.1-rho-ntr-nanoluc-my17-dsred2 prepared in Example 1, transgenic zebrafish Tg (rho: NTR-NanoLuc, my17: DsRed2) were prepared by the gene introduction method using I-SceI meganuclease (Soroldoni D, Hogan B. M., Oates AC., "Simple and efficient transgenesis with meganuclease constructs in zebrafish.", Methods Mol. Biol., 2009; 546: 117-130.). The specific procedure was as follows:

1) An injection solution was prepared by blending 1 µL of pcDNA3.1-rho-ntr-nanoluc-my17-dsred2 (712 ng/µL), 1.5 µL of Meganuclease buffer (10X), 0.6 µL of I-SceI (New England Biolab Japan Co., Ltd.; 5,000 units/mL), 1.5 µL of 0.5% phenol red (Sigma-Aldrich Japan) and 10.4 µL of $dH_2O$.

2) To the cytoplasm of a single-cell embryo (fertilized egg) obtained from wild-type zebrafish, the injection solution (1 nL) was injected by use of FemtoJet (registered trademark) (Eppendorf).

3) In the evening of the injection day, the dead eggs were removed. On day 3 after fertilization, a transgenic fish temporarily exhibiting expression was selected under a fluorescence microscope using DsRed2 expression in the heart as an index.

4) The transgenic fish temporarily expressing DsRed2 in the heart was raised until it could lay eggs and crossed with wild-type zebrafish to obtain fertilized eggs. The resulting fertilized eggs were observed under a fluorescence microscope. If a fertilized egg expressing DsRed2 in the heart could be found, it was demonstrated that its parent could pass on the introduced gene to a child. The transgenic fish was isolated as a founder.

5) The juveniles obtained during and after step 4) by crossing the founder with wild type zebrafish are transgenic fish having stable gene expression. The transgenic fish were subjected, as parents, to cross-fertilization, and juvenile transgenic fish were used for the experiment.

[Validation of Evaluation of Rod-Cell Regeneration Induction by Transgenic Zebrafish]
When mRNA expression of the ntr-nanoluc gene in the retinal tissue of juvenile zebrafish was checked by use of an in-situ hybridization method, a clear signal was observed in the outer granule layer of the retina where rod cells are present. Accordingly, it was confirmed that the ntr-nanoluc gene was specifically expressed in a desired tissue, and that a desired recombinant was produced (FIG. 1). FIG. 1 shows a section of a left eyeball of zebrafish. The upper side of the section is the dorsal side of the zebrafish and the lower side is the ventral side thereof. Reference symbol S represents a negative control (sense RNA probe). Expression of the ntr-nanoluc gene was observed in the figure marked with "AS" (antisense RNA probe).

Day 3 after fertilization, the transgenic zebrafish were treated with 10 mM metronidazole (Sigma-Aldrich Japan) for 24 hours and euthanized by adding ethyl 3-aminobenzoate methanesulfonate (Sigma-Aldrich Japan). Luminescence derived from rod cells was measured in accordance with the manual attached to Nano-Glo (registered trademark) Luciferase Assay System (Promega Corporation). As a result, it was confirmed that rod cells were ablated by treatment with 10 mM metronidazole for 24 hours and reduced in number to 13.5% by cell death (FIG. 2). The resultant transgenic ablated fish were washed with rearing water, and a toxic radical derived from metronidazole was removed. Luminescence derived from the rod cells after 24 and 48 hours was measured. As a result, it was confirmed that rod cells are gradually regenerated over 48 hours (FIG. 3).

Example 3

Screening of Compound and Evaluation of Activity of the Hit Compound

1. Screening of Compound
[Procedure]Compounds were subjected to screening by use of transgenic zebrafish obtained in Example 2.
The procedure of the screening was as follows:

1) On the day before collection of eggs, a pair of male and female zebrafish, i.e., a transgenic fish Tg (rho: NTR-NanoLuc, my17: DsRed2) and a wild type, were placed in a tank for mating and isolated by a divider.

2) The next morning (8:00-11:00), the divider was removed to allow them to mate with each other. Fertilized eggs were collected. In the evening (16:00-18:00) of the same day, only normally developed fertilized eggs were screened and raised in a plate for growth.

3) Day 3 after fertilization, juvenile fish were transferred to rearing water, which contained 10 mM metronidazole (Sigma-Aldrich, Japan) and 1% DMSO (Wako Pure Chemical Industries Ltd.), (prepared by dissolving 60 mg of instant ocean (Napco Limited (Japan)) in 1 L of distilled water), and raised in dark conditions for 24 hours. In this manner, ablation was specifically applied to the rod cells of the juvenile fish. In contrast, non-ablated juvenile fish, which were to be used as a control, were transferred to a tank containing rearing water, which contained a 1% DMSO solution, and raised.

4) In an assay plate (Tissue Culture Treated Black Isoplate-96 TC (PerkinElmer Co., Ltd. Japan) was used), a test compound and DMSO serving as a control were each dispensed in an amount of 2.5 µL/well, and further, Egg water was added in an amount of 147.5 µL/well.

5) Ablated juvenile fish of 4 days after fertilization were washed well with Egg water and dispensed in wells of the assay plate containing a compound together with 100 µL of Egg water, such that 2 juvenile fish individuals were present per well.

6) After the juvenile fish were raised for 2 days, 200 μL of Egg water was removed and ethyl 3-aminobenzoate methanesulfonate (Sigma-Aldrich Japan; 0.4 mg/mL, 10 μL) was added to euthanize the fish.

7) Nano-Glo (registered trademark) Luciferase assay Substrate (Promega Corporation) was added to Nano-Glo (registered trademark) Luciferase assay buffer (Promega Corporation) in a ratio of 1:50 and 100 μL of the resultant solution was added to each of the wells.

8) Shaking was carried out by use of BIO-Mixer (Biotech Japan Co., Ltd.) for one hour and luminescence of NanoLuc (registered trademark) was measured by use of EnVision (PerkinElmer Co., Ltd., Japan).

[Results]

The activation rate (referred to as Activation (%)) of Luciferase by compound stimulation was calculated in accordance with the following expression.

Activation (%)=(measurement value of sample well÷average value of DMSO control)×100

As a result of the above screening, 4-[(E)-2-(5,6,7,8-tetrahydro-5,5,8,8-tetramethyl-2-naphthalenyl)-1-propenyl]benzoic acid (TTNPB) represented by the following formula exhibited an Activation (%) of 150 or more at an effective working concentration of 2.5 μM.

[Formula 1]

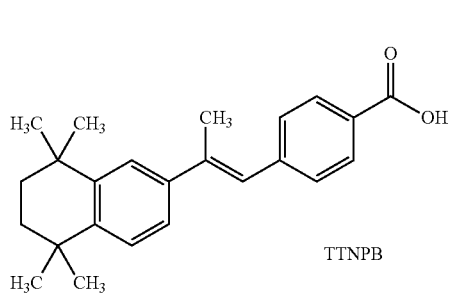

TTNPB

2. Evaluation of Activity of the Hit Compound

[Procedure]

An evaluation test for the rod-cell regeneration induction effect of a screened compound, i.e., TTNPB, at effective working concentrations of 0.3, 1, 3, 10 and 30 μM, was carried out in the same manner as in Section 1 above and repeated 4 times (N=4).

[Data Processing Method]

Data processing was carried out by use of Microsoft Excel 2010 (Microsoft Japan Co., Ltd.). Dunnett's multiple comparison test was carried out by SAS9.3 for Microsoft Windows Workstation 32-bit and the cooperative system EXSUS Ver. 8.0.

In the evaluation of the rod-cell regeneration induction activity of the compound, the activation rate (referred to as Activation (%)) of Luciferase by a compound stimulation was calculated in accordance with the following expression and an average value and standard error were displayed.

Activation (%)=(Measurement value of sample well÷average value of DMSO control)×100

Individual concentration groups were compared to the DMSO control group by the Dunnett's test.

[Results]

The results are shown in FIG. 4. TTNPB showed a statistically significant rod-cell regeneration induction activity at all concentrations compared to the DMSO control; however, concentration dependency was not observed within the concentration range of the test. From this, it was considered that the medicinal effect of TTNPB already reached a saturation at a minimum concentration of 0.3 μM.

Example 4

Validation of Relevance Between RAR Agonistic Activity and Rod-Cell Regeneration Induction Activity

[Procedure]

From the results of Example 3, it was found that TTNPB has a rod-cell regeneration induction activity. TTNPB is known as an RAR agonist. Then, validation of compounds known to act on RAR was carried out. The verification test was carried out in accordance with the procedure of Example 3 "1. Screening of compound" in N=8.

Compounds to be verified are an endogenous retinoic acid receptor agonist, All-trans Retinoic acid (Sigma-Aldrich, Cat. No. R2625-50MG) and an RAR antagonist, BMS493 (Sigma-Aldrich, Cat. No. B6688-5MG). The chemical structures of them are shown below:

[Formula 2]

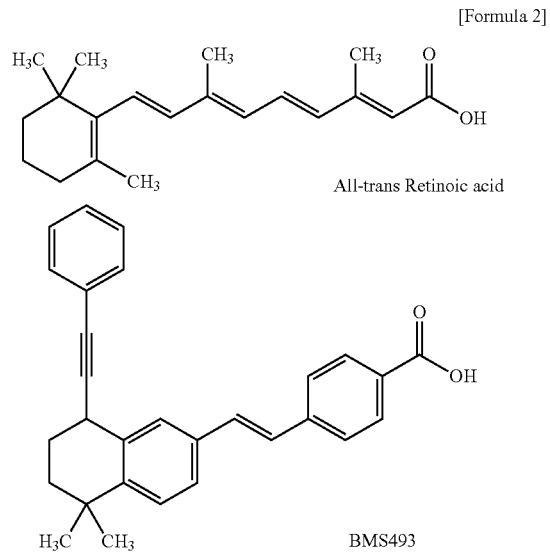

[Data Processing Method]

Data processing was carried out by use of Microsoft Excel 2010 (Microsoft Japan Co., Ltd.). Dunnett's multiple comparison test was carried out by SAS9.3 for Microsoft Windows Workstation 32-bit and the cooperative system EXSUS Ver. 8.0. In the evaluation of the rod-cell regeneration activity, the activation rate (referred to as Activation (%)) of Luciferase by a compound stimulation was calculated in accordance with the following expression, and an average value and standard error were displayed.

Activation (%)=(Measurement value of sample well÷average value of DMSO control)×100

[Results]

The results of Example 5 are shown in FIG. 5. An endogenous RAR agonist, All-trans Retinoic acid (RA), showed a significant rod-cell regeneration induction activity in a concentration-dependent manner; whereas, BMS493 inhibiting RAR did not show rod-cell regeneration induction activity and the value thereof was lower than that of the DMSO control. In the case of BMS493, the compound precipitated at a concentration of 30 μM and all fish died (of cardiac arrest) at a concentration of 100 μM. BMS493 was found to be toxic.

Example 5

Method for Measuring RAR Agonistic Activity

[Procedure]

RAR agonistic activity was measured in the following procedure. The compounds used for evaluation were tamibarotene (Combi-Blocks, Cat. No. QA-6963), tamibarotene methyl ester (Sundia meditech, Cat. No. 82569), tamibarotene ethyl ester (described in Org. Lett., 15, 3678-3681 (2013)), tazarotene (Tokyo Kasei, Cat. No. T3108), tazarotenic acid (obtained by hydrolysis of tazarotene with reference to the method described in U.S. Pat. No. 6,344,463), adapalene (Tokyo Kasei, Cat. No. 2549) and palovarotene (Haoyuan Chemexpress Co., Ltd., Cat. No. HY-14799).

1) HEK293A cells (Invitrogen), which functionally co-express Human RARα, Human RARβ and Human RARγ, were prepared by adding Lipofectamine (registered trademark) 2000 Transfection Reagent (Thermo Fisher Scientific) to an RAR synthetic response element luciferase reporter construct (3xDR5: luc) in accordance with the method described in the manual attached to the kit. The genes introduced are shown in Table 1.

2) The cells having the genes introduced therein were recovered and seeded in a 384-well Plate so as to obtain $2 \times 10^5$ cells/mL; at the same time, the cells were allowed to be contacted with a compound (4-fold serial dilution was repeated 10 times from a maximum concentration of 25000 nM).

3) Twenty-four hours after exposure to a compound, luminescence from the cells was measured by using PICCA JEAN (registered trademark) luminescence kit (TOYO B-Net CO., LTD.) and EnVision (PerkinElmer Corporation, Japan) (N=4).

[Analysis]

Average value and EC of luminescence (cps) were calculated by use of Microsoft Excel 2010.

[Data Processing]

In evaluation of RAR agonistic activity, provided that the measurement value (Negative control) of luminescence from the cells with no addition of a compound was determined as 100%, the RAR agonistic activity (%) of a test substance was calculated in accordance with the following expression. The average value thereof was plotted versus the concentration of a test substance.

RAR agonistic activity (%)=(measurement value of sample well÷average value of Negative control)×100

The index for the intensity of RAR agonistic activity was defined as follows: for RARα and RARβ, the concentration exhibiting an amount of luminescence of 1000% was defined as $EC_{1000}$ based on the luminescence of the Negative control; whereas for RARγ, the concentration exhibiting an amount of luminescence of 500% was defined as $EC_{500}$ based on the luminescence of the Negative control. $EC_{1000}$ or $EC_{500}$ was calculated based on the GROWTH function (exponential regression) by using concentrations at two points either side of a point exhibiting an amount of luminescence and RAR agonistic activity (%) by the test substance of 1000% or 500%.

[Results]

The measurement results of the compounds of Example 5 are shown in Table 2. The compounds exhibited agonist activities to any one of RARs in a concentration dependent manner.

TABLE 1

|  | Human RARα | Human RARβ | Human RARγ |
|---|---|---|---|
| Protein | retinoic acid receptor alpha | retinoic acid receptor beta | retinoic acid receptor gamma |
| Gene | RARA | RARB | RARG |
| Type | DNA | DNA | DNA |
| Origin | Homo sapiens | Homo sapiens | Homo sapiens |
| Sequence | SEQ ID NO: 5 | SEQ ID NO: 6 | SEQ ID NO: 7 |

TABLE 2

|  | RARα EC1000 (nM) | RARβ EC1000 (nM) | RARγ EC500 (nM) |
|---|---|---|---|
| Tamibarotene | 1.9 | 79 | 248 |
| Tamibarotene methyl ester | 0.91 | 29.1 | 72.8 |
| Tamibarotene ethyl ester | 21.8 | 514 | 714 |
| Tazarotene | 115 | 32 | 1858 |
| Tazarotenic acid | 12 | 4.4 | 48 |
| Adapalene | 12 | 6.9 | 54 |
| Palovarotene | 101 | 132 | 34.9 |

Example 6

Evaluation of Rod-Cell Regeneration Induction Effect of Various RAR Agonists

[Procedure]

The rod-cell regeneration induction activity of compounds exhibiting RAR agonistic activity was evaluated in the following procedures. Based on evaluation, generality was verified. The compounds used for evaluation were tamibarotene (Combi-Blocks, Cat. No. QA-6963), tamibarotene methyl ester (Sundia meditech, Cat. No. 82569), tamibarotene ethyl ester (described in Org. Lett., 15, 3678-3681 (2013)), tazarotene (Tokyo Kasei, Cat. No. T3108), tazarotenic acid (obtained by hydrolysis of tazarotene with reference to the method described in U.S. Pat. No. 6,344,463), adapalene (Tokyo Kasei, Cat. No. 2549) and palovarotene (Haoyuan Chemexpress Co., Ltd., Cat. No. HY-14799).

1) On the day before collection of eggs, a pair of male and female zebrafish, i.e., a transgenic fish Tg (rho: NTR-NanoLuc, my17: DsRed2) and a wild type, were placed in a tank for cross-fertilization and isolated by a divider.

2) The next morning (8:00-11:00), the divider was removed to allow them to mate with each other. Fertilized eggs were collected. In the evening (16:00-18:00) of the same day, only normally developed fertilized eggs were screened and raised in a plate for growth.

3) Day 3 after fertilization, juvenile fish were transferred to rearing water, which contained 10 mM metronidazole (Sigma-Aldrich, Japan) and 1% DMSO (Wako Pure Chemical Industries Ltd.), (prepared by dissolving 60 mg of instant ocean (Napco Limited (Japan)) in 1 L of distilled water) and raised in dark conditions for 24 hours. In this manner, ablation was specifically applied to the rod cells of the juvenile fish. In contrast, non-ablated juvenile fish, which were to be used as a control, were transferred to a tank containing rearing water, which contained a 1% DMSO solution, and raised.

4) In an assay plate (Tissue Culture Treated Black Isoplate-96 TC (PerkinElmer Co., Ltd. Japan) was used), a test compound, which was serially diluted so as to obtain data at two concentrations either side of 50%, and DMSO serving as a control were each dispensed in an amount of 2.5 μL/well and further Egg water was added in an amount of 147.5 μL/well.

5) Ablated juvenile fish of Day 4 after fertilization were washed well with Egg water and dispensed in wells of the assay plate containing a compound together with 100 μL of Egg water such that 2 juvenile fish individuals were present per well.

6) After the juvenile fish were raised for 2 days, 200 μL of Egg water was removed and ethyl 3-aminobenzoate methanesulfonate (Sigma-Aldrich Japan; 0.4 mg/mL, 10 μL) was added to euthanize.

7) Nano-Glo (registered trademark) Luciferase assay Substrate (Promega Corporation) was added to Nano-Glo (registered trademark) Luciferase assay buffer (Promega Corporation) in a ratio of 1:50 and 100 μL of the resultant solution was added to each of the wells.

8) Shaking was carried out by use of BIO-Mixer (Biotech Japan Co., Ltd.) for one hour, and luminescence of NanoLuc (registered trademark) was measured by use of EnVision (PerkinElmer Co., Ltd. Japan).

[Analysis]

The increase rate (referred to as Activation (%)) of Luciferase activity and an average value and $EC_{50}$ were calculated by Microsoft Excel 2010.

[Data Processing]

In evaluating rod-cell regeneration activity, provided that the measurement value of the luminescence from zebrafish treated with DMSO (compound of a negative control) was specified as 0%, whereas the measurement value of the luminescence from zebrafish treated with 1 μM TTNPB (a compound of a positive control) is specified as 100%, Activation (% of control) was calculated as an index of activity in accordance with the following expression and an average value thereof was plotted versus concentration of a test substance. The concentration at which Activation (% of control) 50% was exhibited was defined as $EC_{50}$. $EC_{50}$ was calculated by linear regression between 2 points either side of a point exhibiting a test-substance activity of 50%.

Activation (% of control)=(measurement value of Sample well−average value of Negative control)÷(average value of Positive control−average value of Negative control)×100

[Results]

The test results of Example 6 are shown in Table 3. All RAR agonists exhibited significant regeneration induction activity in a concentration dependent manner. Note that the value of Adapalene with an asterisk means that Activation (% of control) at a concentration of 1000 nM (the maximum concentration evaluated) failed to reach 50%. The activation at the concentration was 39%. Of the RAR agonists evaluated, tamibarotene and tamibarotene ethyl ester exhibited a strong rod-cell regeneration induction activity.

TABLE 3

| Name | Structure | EC50 (nM) |
|---|---|---|
| Tamibarotene | 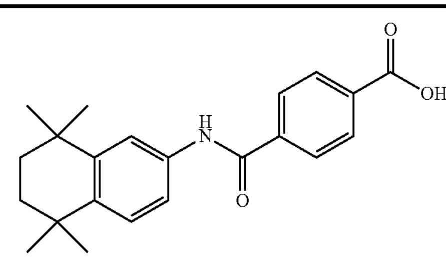 | 9.08 |
| Tazarotene | 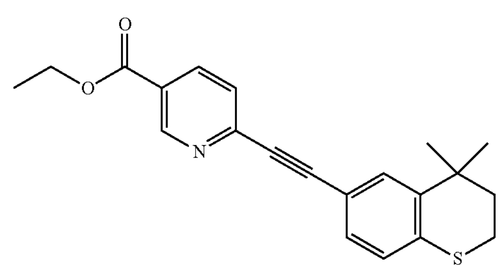 [SMILES: CCOC(=O)c1ccc(C#Cc2ccc3c(c2)C(C)(C)CCS3)nc1] | 402 |
| Tamibarotene methyl ester | 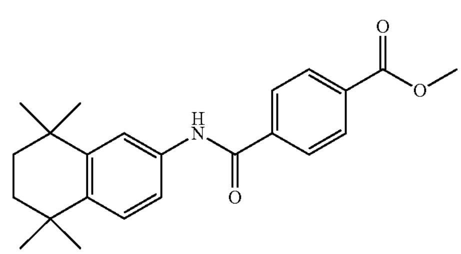 [SMILES: COC(=O)c1ccc(C(=O)Nc2ccc3c(c2)C(C)(C)CCC3(C)C)cc1] | 85.4 |

TABLE 3-continued

| Name | Structure | EC50 (nM) |
|---|---|---|
| Tazarotenic acid | 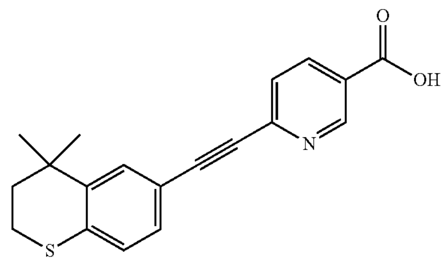 [SMILES: CC1(C)CCSc2ccc(C#Cc3ccc(C(=O)O)cn3)cc21] | 786 |
| Tamibarotene ethyl ester | 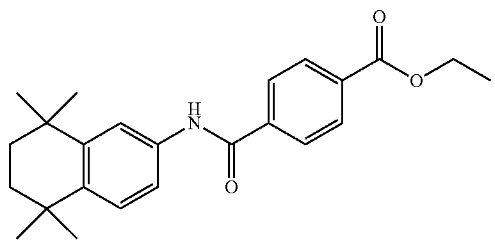 [SMILES: CCOC(=O)c1ccc(C(=O)Nc2ccc3c(c2)C(C)(C)CCC3(C)C)cc1] | 4.90 |
| Adapalene | 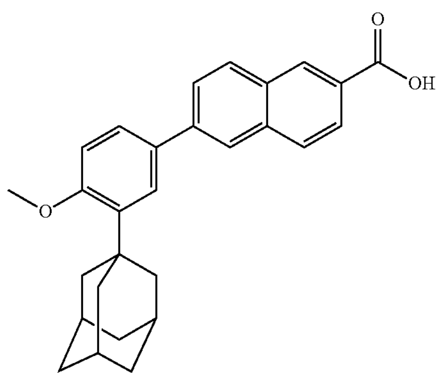 [SMILES: COc1ccc(-c2ccc3cc(C(=O)O)ccc3c2)cc1C12CC3CC(CC(C3)C1)C2] | >1000* |
| Palovarotene | 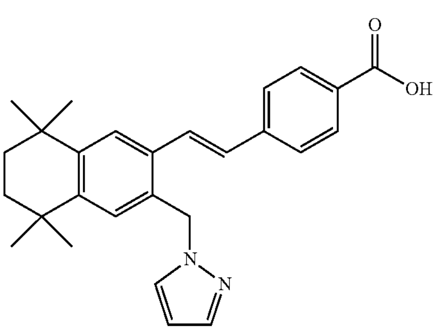 [SMILES: CC1(C)CCC(C)(C)c2cc(Cn3cccn3)c(/C=C/c3ccc(C(=O)O)cc3)cc21] | 1210 |

Example 7

Evaluation of the Rod-Cell Regeneration Effect in Retinitis Pigmentosa Model (Confirmation of Effect)

Pathological model fish, in which rod-cell regeneration can be observed, were prepared using zebrafish known as a retinitis pigmentosa model. The effect of a compound was confirmed in accordance with the following procedure. As the compound to be evaluated, TTNPB (Sigma-Aldrich, Cat. No. T3757-10MG), was used.

[Preparation of Pathological Model Zebrafish in Which Rod-Cell Regeneration can be Observed]

1) To prepare a pathological model, in which rod-cell regeneration can be observed, zebrafish Tg (rho: EGFP) (Hamaoka T1, Takechi M, Chinen A et al., Visualization of rod photoreceptor development using GFP-transgenic zebrafish. Genesis. 2002; 34 (3): 215-220.; used as a reporter fish of rod cells) were crossed with zebrafish Tg (rho: hRHO (Q344X), omp: EGFP), which is a name under another nomenclature system of a retinitis pigmentosa model, i.e., zebrafish RH1: hRhodopsin (Q344X) (Nakao T, Tsujikawa M, Notomi S, Ikeda Y, Nishida K., "The role of mislocalized phototransduction in photoreceptor cell death of retinitis pigmentosa.", PLoS One., 2012; 7 (4): e32472). The zebrafish obtained were specified as zebrafish (Pathological zebrafish 1). Control zebrafish (non-pathological zebrafish) were obtained by crossing zebrafish Tg (rho: EGFP) with wild-type zebrafish. On the day before collection of eggs, male and female zebrafish were placed in a tank for crossing and isolated by a divider.

2) The next morning (8:00-11:00), the divider was removed to allow them to mate with each other. Fertilized eggs were collected. In the evening (16:00-18:00) of the same day, only normally developed fertilized eggs were screened and raised in a plate for growth.

3) In an assay plate, a test compound and DMSO used as a control were both dispensed in an amount of 2.5 µL/well (DMSO final concentration 1%), and further, Egg water was added in an amount of 147.5 µL/well. A screening test was repeated 8 times (N=8) at each concentration.

4) Juvenile fish of Day 3 after fertilization were dispensed such that 2 juvenile fish individuals were present per well of an assay plate containing a compound, together with 100 µL of Egg water.

5) After the juvenile fish were raised for 2 days, 200 µL of Egg water was removed and ethyl 3-aminobenzoate methanesulfonate (Sigma-Aldrich Japan; 0.4 mg/mL, 10 µL) was added to euthanize.

[Confirmation of Rod-Cell Regeneration by Confocal Laser Microscope]

Luminescence of EGFP specifically expressed in rod cells was observed by a confocal laser microscope in the following procedure.

1) The zebrafish euthanized above were transferred to an Eppendorf tube containing a 4% Paraformaldehyde Phosphate Buffer Solution and shaken at 4° C. overnight and immobilized.

2) The immobilized zebrafish were transferred to an Eppendorf tube containing 0.75% SeaPlaque (registered trademark) agarose warmed to dissolve and embedded on a slide glass together with 0.75% SeaPlaque (registered trademark) agarose.

3) After the agarose was solidified, a mounting medium was added and enclosed with a cover glass to prepare a specimen to be observed by a confocal laser microscope.

4) An image taken under a confocal laser microscope was carried out in the following conditions:
Format: 1024×1024
Speed: 400 Hz
Mode: Photon counting
z-step size: 3 µm
z-volume: 250 µm

[Results]

The results are shown in FIG. 6.

(A) shows the results in non-pathological zebrafish (control). (B) shows the results in zebrafish untreated with a drug. Loss of the rod cells was observed in (B) compared to (A). (C) shows the results in pathological zebrafish applied with 1 µM TTNPB. Recovery in the number of rod cells was confirmed in (C) compared to (B).

Example 8

Evaluation of Rod-Cell Regeneration Effect in Retinitis Pigmentosa Model (Quantitative Evaluation)

Pathological model zebrafish, in which rod-cell regeneration can be quantitatively evaluated, were newly prepared using zebrafish known as a retinitis pigmentosa model. The effect of compounds was quantitatively verified in accordance with the following procedure. The compounds used for evaluation were tamibarotene (Combi-Blocks, Cat. No. QA-6963) and TTNPB (Sigma-Aldrich, Cat. No. T3757-10MG).

[Preparation of Pathological Model Fish in which Quantitative Evaluation can be Made and Procedure for Evaluation of Compound]

1) Quantitative evaluation of rod-cell regeneration was carried out by zebrafish (pathological zebrafish 2) obtained by crossing transgenic Tg (rho: NTR-NanoLuc, my17: DsRed2) and Tg (rho: hRHO (Q344X), omp: EGFP). On the day before collection of eggs, male and female zebrafish were placed in a tank for cross-fertilization and isolated by a divider.

2) The next morning (8:00-11:00), the divider was removed to allow them to mate with each other. Fertilized eggs were collected. In the evening (16:00-18:00) of the same day, only normally developed fertilized eggs were screened and raised in a plate for growth.

3) In an assay plate, a test compound and DMSO serving as a control were each added in an amount of 2.5 µL/well (DMSO final concentration: 1%) and further Egg water was added in an amount of 147.5 µL/well. A screening test was repeated 8 times (N=8) at each concentration.

4) Juvenile fish of Day 3 after fertilization were dispensed such that 2 juvenile fish individuals were present per well of an assay plate containing a compound, together with 100 µL of Egg water.

5) After the juvenile fish were raised for 2 days, 200 µL of Egg water was removed and ethyl 3-aminobenzoate methanesulfonate (Sigma-Aldrich Japan; 0.4 mg/mL, 10 µL) was added to euthanize.

[Quantitative Evaluation of Rod-Cell Regeneration]

1) Nano-Glo (registered trademark) Luciferase assay Substrate was added to Nano-Glo (registered trademark) Luciferase assay buffer in a ratio of 1:50 and the mixture was added to individual wells of the plate prepared in accordance with Example 3, in an amount of 100 µL per well.

2) After shaking for one hour using BIO-Mixer, the luminescence from NanoLuc (registered trademark) was measured by use of EnVision.

[Analysis]

Data processing was carried out by use of Microsoft Excel 2010 (Microsoft Japan Co., Ltd.). A Dunnett's multiple comparison test was carried out by use of SAS9.3 for Microsoft Windows Workstation 32-bit and the cooperative system EXSUS Ver. 8.0.

The average value and standard error of luminescence (cps, count per second) were calculated and displayed.

[Results]

It was confirmed that TTNPB and tamibarotene both induce statistically significant regeneration of rod cells in a dose dependent manner in the retinitis pigmentosa model (FIG. 7).

Preparation Example 1

Liquid Preparation

Tamibarotene (6 g), dextrose monohydrate (appropriate amount to obtain isotonicity), citric acid monohydrate (1.05 g), sodium hydroxide (0.18 g) and water for injection (appropriate amount until the entire solution reaches 1000 mL) are mixed in accordance with a routine method.

Preparation Example 2

Eye Ointment

To tamibarotene (0.6 g), an appropriate amount of liquid paraffin is added and mixed. To the mixture, ophthalmic vaseline is added such that the total amount reaches 100 g and mixed.

INDUSTRIAL APPLICABILITY

The number of rod cells can be increased by inducing rod-cell regeneration by adding a compound having a retinoic acid receptor agonistic activity, with the result that retinitis pigmentosa, etc., can be simply treated and/or prevented. The compound is useful as a medicine.

Sequence Listing Free Text

SEQ ID NO: 1: Nucleotide sequence of rho promoter site of zebrafish
SEQ ID NO: 2: Nucleotide sequence of my17 promoter site of zebrafish
SEQ ID NO: 3: Nucleotide sequence of NTR-NanoLuc protein
SEQ ID NO: 4: Nucleotide sequence of DsRed2 protein
SEQ ID NO: 5: Nucleotide sequence of human RARα
SEQ ID NO: 6: Nucleotide sequence of human RARβ
SEQ ID NO: 7: Nucleotide sequence of human RARγ

The invention claimed is:

1. A method for treating retinitis pigmentosa, comprising administering tamibarotene or tamibarotene ethyl ester, or a salt thereof.

2. The method according to claim 1, wherein the method comprises administering tamibarotene.

3. The method according to claim 1, wherein tamibarotene or tamibarotene ethyl ester, or the salt thereof, is topically administered to the eye.

* * * * *